(12) United States Patent
Lu et al.

(10) Patent No.: US 11,076,870 B2
(45) Date of Patent: Aug. 3, 2021

(54) SPINAL REAMING APPARATUS

(71) Applicants: WILTROM CO., LTD., Zhubei (TW); GROUP INNOMED BIOTECH CO., LTD., Taipei (TW)

(72) Inventors: Chieh-Feng Lu, Zhubei (TW); Chang-Ho Tseng, Zhubei (TW); Meng-Yuan Tsai, Zhubei (TW); Huang-Chien Liang, Zhubei (TW)

(73) Assignee: Wiltrom Co., Ltd., Zhubei (TW)

(*) Notice: Subject to any disclaimer, the term of this patent is extended or adjusted under 35 U.S.C. 154(b) by 239 days.

(21) Appl. No.: 16/394,746

(22) Filed: Apr. 25, 2019

(65) Prior Publication Data
US 2019/0328406 A1    Oct. 31, 2019

(30) Foreign Application Priority Data
Apr. 26, 2018   (TW) .................................. 107114238

(51) Int. Cl.
*A61B 17/16* (2006.01)
*A61B 17/00* (2006.01)

(52) U.S. Cl.
CPC ...... *A61B 17/1671* (2013.01); *A61B 17/1615* (2013.01); *A61B 17/1617* (2013.01); *A61B 17/1631* (2013.01); *A61B 17/1633* (2013.01); *A61B 2017/00738* (2013.01)

(58) Field of Classification Search
CPC ............. A61B 17/1617; A61B 17/1671; B23B 51/0036; B23B 51/102
See application file for complete search history.

(56) References Cited

U.S. PATENT DOCUMENTS

| | | | | |
|---|---|---|---|---|
| 1,858,852 A | * | 5/1932 | Cleveland | B23B 29/03453 82/1.2 |
| 2,404,027 A | * | 7/1946 | Belanger | B23B 51/102 408/159 |
| 2,461,947 A | * | 2/1949 | Weber | B23B 51/0036 82/1.2 |
| 3,318,175 A | * | 5/1967 | Cogsdill | B23B 51/102 408/159 |
| 3,372,610 A | * | 3/1968 | Johansson | B23B 51/102 408/199 |
| 3,407,703 A | * | 10/1968 | Vinzenz | B23B 51/102 409/191 |

(Continued)

FOREIGN PATENT DOCUMENTS

| | | |
|---|---|---|
| CN | 103919594 A | 7/2014 |
| GB | 2483089 A | 2/2012 |

*Primary Examiner* — David W Bates
(74) *Attorney, Agent, or Firm* — Muncy, Geissler, Olds & Lowe, P.C.

(57) ABSTRACT

Provided is a spinal reaming apparatus including a sleeve, an eccentric shaft, an operated element and an eccentric reaming element. The sleeve has a first end and a second end opposing the first end. The eccentric shaft is received in the sleeve. The operated element is connected to the eccentric shaft and positioned proximate to the first end of the sleeve. The eccentric reaming element is connected to the eccentric shaft and disposed at the second end of the sleeve. When rotated, the operated element drives the eccentric reaming element to rotate relative to the sleeve on the eccentric shaft such that the spinal reaming apparatus will switch between a folded mode and a functioning mode.

17 Claims, 21 Drawing Sheets

(56) References Cited

U.S. PATENT DOCUMENTS

| | | | | |
|---|---|---|---|---|
| 3,540,324 A * | 11/1970 | Johansson | B23B 51/102 | 408/227 |
| 3,690,357 A * | 9/1972 | Roberto Lugo | B27G 13/14 | 144/232 |
| 3,806,271 A * | 4/1974 | Ishiguro | B23B 51/102 | 408/159 |
| 3,814,535 A * | 6/1974 | Steiner | B23B 51/102 | 408/73 |
| 3,827,821 A * | 8/1974 | Swenson | B23B 51/102 | 408/59 |
| 4,700,789 A * | 10/1987 | Velasco | B23B 51/0036 | 175/202 |
| 4,710,070 A * | 12/1987 | Alsen | B23B 51/102 | 408/187 |
| 4,930,585 A * | 6/1990 | Noser | B23B 51/0036 | 175/202 |
| 5,020,613 A * | 6/1991 | Bergner | B23B 51/0036 | 175/273 |
| 5,036,928 A * | 8/1991 | Mark | B23B 51/0036 | 175/263 |
| 5,076,743 A * | 12/1991 | Mark | B23B 29/03485 | 408/151 |
| 5,445,639 A * | 8/1995 | Kuslich | A61B 17/1671 | 606/180 |
| 5,839,860 A * | 11/1998 | Steiner | B23B 51/102 | 408/180 |
| 6,447,513 B1 * | 9/2002 | Griggs | A61B 17/7266 | 606/62 |
| 6,814,734 B2 * | 11/2004 | Chappuis | A61B 17/1617 | 606/180 |
| 9,028,499 B2 * | 5/2015 | Keyak | A61K 51/1203 | 606/79 |
| 9,089,905 B1 * | 7/2015 | Craig | B23B 51/08 | |
| 2004/0005200 A1 * | 1/2004 | Heule | B23B 51/102 | 408/173 |
| 2004/0126196 A1 * | 7/2004 | Burr | B23B 51/102 | 408/187 |
| 2004/0208717 A1 * | 10/2004 | Greenhalgh | B23B 51/0045 | 408/224 |
| 2007/0276392 A1 | 11/2007 | Beyar et al. | | |
| 2010/0331846 A1 * | 12/2010 | Malawar | A61B 17/1617 | 606/80 |
| 2013/0115019 A1 * | 5/2013 | Studer | B23B 51/102 | 408/57 |
| 2016/0038157 A1 * | 2/2016 | Mirochinik | A61B 17/1796 | 606/80 |

* cited by examiner

FIG. 6A
FIG. 6B
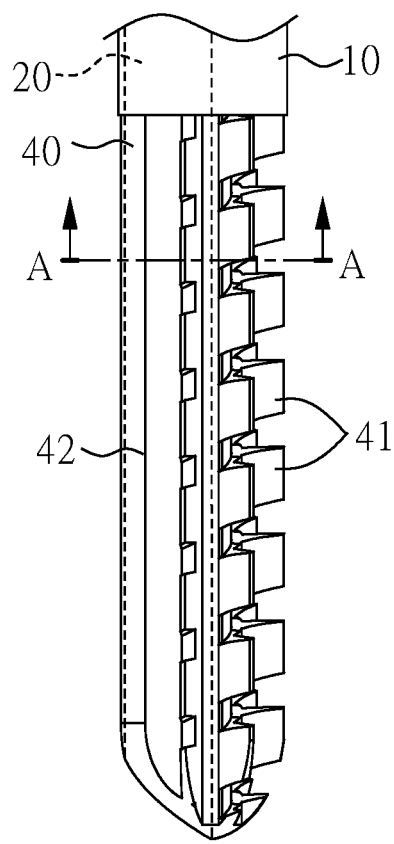
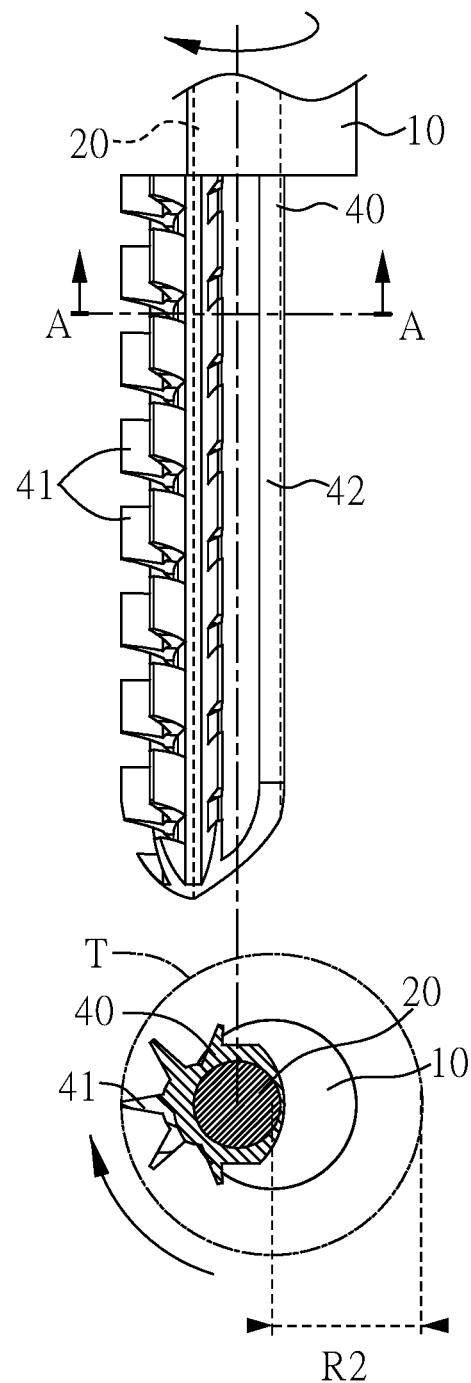
FIG. 7A
FIG. 7B
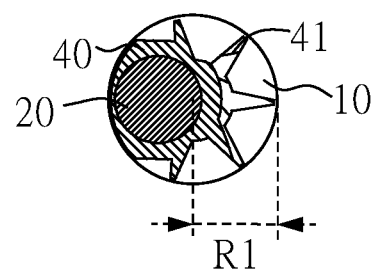
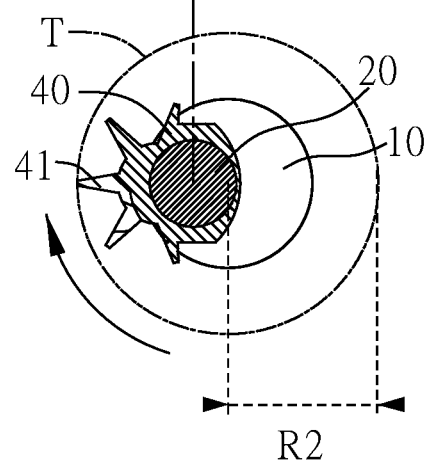

__SPINAL REAMING APPARATUS__

BACKGROUND

1. Technical Field

The present disclosure relates to reamer and, more particularly, to a vertebral reamer for use in spinal surgery.

2. Description of the Related Art

The spine is a major component of the central nervous system of the human body. Spinal disorders often have a considerable impact on patients, causing pain, numbness, weakness, and even incontinence, dysuria, dyschezia, or other symptoms. The above symptoms are caused by a translocation between adjacent vertebral bodies and thus to oppress nerves or spinal cords. Due to their different mechanisms, spinal disorders are clinically diagnosed as disc herniation, spondylolisthesis, spinal stenosis or degenerative scoliosis. When symptoms are severe, the discomfort of patients usually cannot be relieved by spinal correction, and spinal surgery is required to restoration the vertebrae.

FIG. 1A and FIG. 1B are schematic views of an implant for performing vertebrae restoration by spinal surgery. FIG. 1A illustrates its folded mode. FIG. 1B illustrates its expanded mode. Regarding vertebra dislocation caused by collapse, such as spinal compression fracture caused by osteoporosis, the existing surgical procedure which poses the best therapeutic efficacy is to place an implant 9 into the cancellous bone of the vertebra in the folded mode, after which the implant 9 is turned to the expanded mode, in which the vertebra is stretched to restore it to a specific height such that bone cement has a sufficient space to fill. After the bone cement has solidified, the spinal restoration of the vertebra is done.

The surgery requires the surgeon to create a hole at a planned pedicle entry point on a vertebra with an awl and thereby to bore out a channel passing through a pedicle to the cancellous bone. However, the diameter of said channel is usually too small for the implant 9 to pass through. As a result, said channel has to be reamed with a bone drill or a surgical drill in order for the implant 9 to pass through said channel and thereby reach the body.

To address the aforesaid issue, instrument manufacturers usually provide an instrument kit including an awl, bone drill or surgical drill with larger outer diameters to enable surgeons to form an implanting channel of a large inner diameter with the instruments in a one-time surgical procedure. However, this surgical procedure is not a priority procedure, as the success of the surgical procedure relies on the surgeons' clinical expertise, and in consequence, the risks are that the implanting channel will deviate and thus be exposed from the pedicle (commonly known as a rupture). Therefore, most surgeons prefer an instrument change approach, i.e., to gradually expand the implanting channel by using instruments with larger and larger outer diameters and thus reduce surgical risks. Nonetheless, the use of a reaming instrument of a large outer diameter might increase the risk of a rupture, and the complicated procedure of changing reaming instruments also prolongs the surgery, to the detriment of the patient's prognosis.

As a result, it is difficult to balance the limitations of an outer diameter of a reaming instrument and the risk of a rupture. For instance, the lumbar pedicles being just around 10 mm wide, so to reduce the risk of a rupture, safety-conscious surgeons always use a bone drill or a surgical drill having a maximum outer diameter of seldom greater than 6.5 to 7 mm; as a result, the maximum diameter of the reamed implanting channel is confined to the range of 6.5 mm to 7 mm. This poses a challenge to orthopedic surgeons whenever the implant 9 requires an implanting channel of a diameter greater than 8 mm to ensure sufficient room for manipulation.

Therefore, it is imperative to provide a spinal reaming apparatus which can not only pass through an anatomically narrow structure, such as the pedicle, in a safe manner in terms of size (for example, with an inner diameter of around 6.5 mm or less to one of 7 mm) but also expands to a larger size at an anatomically recipient position, such as at a target position of the cancellous bone in the vertebra, so as to create additional space for following procedure.

SUMMARY

In view of the aforesaid drawbacks of the prior art, it is an objective of the present disclosure to provide a spinal reaming apparatus which comprises an eccentric shaft and an eccentric reaming element, such that the spinal reaming apparatus operates in a size-dependable folded mode and a size-expandable functioning mode is able to not only pass through an anatomically narrow structure, such as the pedicle, in the folded mode but also perform a reaming procedure in an anatomically recipient structure, such as the cancellous bone in the vertebra, in the functioning mode which is larger in terms of size, thereby reducing the risk of a rupture, which otherwise would be caused by any large surgical instrument.

In order to achieve the above and other objectives, the present disclosure provides a spinal reaming apparatus comprising a sleeve, an eccentric shaft, an operated element and an eccentric reaming element. The sleeve has a first end and a second end opposing the first end. The eccentric shaft is disposed in the sleeve. The operated element is connected to the eccentric shaft and positioned proximate to the first end of the sleeve. The eccentric reaming element is connected to the eccentric shaft and disposed at the second end of the sleeve. When the operated element is rotated, the operated element drives the eccentric reaming element to rotate relative to the sleeve on the eccentric shaft such that the spinal reaming apparatus can switch between a folded mode and a functioning mode.

In the embodiments of the present disclosure, the adjective "eccentric" is descriptive of a component situated away from the axis of the sleeve. The eccentric shaft, for example, is described as eccentric because the projection of the center of its cross section does not fall on (i.e., overlap) the center of the cross section of the sleeve. Alternatively, "eccentric" is descriptive of the axis of the eccentric shaft, which is parallel to (rather than overlaps) the axis of the sleeve, and the distance therebetween is known as the eccentric distance. As for the eccentric reaming element, the point at which it connects to the eccentric shaft is the center of rotation with the eccentric shaft as a pivot, and its projection does not fall on (i.e., overlap) the center of the cross section of the sleeve. In an embodiment of the present disclosure, when the eccentric shaft, eccentric reaming element and sleeve are cylinders, the projection of the axial center of the eccentric shaft as well as the projection of the middle point of the connection of the eccentric reaming element and the eccentric shaft do not fall on (i.e., overlap) the axial center of the sleeve, and thereby they are considered as eccentric. Similarly, the axis of the eccentric shaft is parallel to (rather than overlaps) the axis of the eccentric reaming element, and thus there is an eccentric distance therebetween. The technical feature "eccentric" disclosed in the present disclosure is not restricted to all aspects of the embodiments of the present disclosure, and thus every other geometric shape shall be deemed to fall within the scope of the present disclosure, provided that the geometric shape is identical or similar to its counterparts disclosed in all aspects of the embodiments of the present disclosure in terms of technical concepts. For example, the sleeve and/or the eccentric reaming element are/is a hexagonal prism, octagonal prism or dodecagonal prism.

According to an embodiment of the present disclosure, the eccentric reaming element rotates eccentrically and relative to the sleeve with the eccentric shaft as a pivot.

According to an embodiment of the present disclosure, the eccentric reaming element is flush with the sleeve substantially in the folded mode, and the eccentric reaming element protrudes from the sleeve in the functioning mode.

According to an embodiment of the present disclosure, an outer diameter of the eccentric reaming element is substantially equal to an outer diameter of the sleeve.

According to an embodiment of the present disclosure, the eccentric reaming element is of a first radius, and when the spinal reaming apparatus rotates a complete turn in the functioning mode, a second radius of a circular trajectory is formed by the eccentric reaming element, and the second radius is greater than the first radius.

According to an embodiment of the present disclosure, the operated element is rotated by 90 degrees or 180 degrees such that the spinal reaming apparatus switches between the folded mode and the functioning mode.

According to an embodiment of the present disclosure, the spinal reaming apparatus further comprises a gripping element disposed at the first end of the sleeve and between the sleeve and the operated element.

According to an embodiment of the present disclosure, the eccentric shaft passes through the gripping element to connect to the operated element.

According to an embodiment of the present disclosure, the operated element comprises a fastening unit for fixing a position of the operated element relative to the gripping element.

According to an embodiment of the present disclosure, the operated element comprises a first positioning portion, and the gripping element comprises two second positioning portions, such that the first positioning portion can move from one of the two second positioning portions to the other said second positioning portion and engage therewith as soon as the operated element is rotated.

According to an embodiment of the present disclosure, the gripping element comprises a guide groove, the two second positioning portions are disposed at two opposing ends of the guide groove, respectively, and the first positioning portion moves along the guide groove when the operated element is rotated.

According to an embodiment of the present disclosure, the first positioning portion comprises a pin and a lever, and the two second positioning portions are each a recess.

According to an embodiment of the present disclosure, the eccentric reaming element is covered with a plurality of cutting portions.

According to an embodiment of the present disclosure, the spinal reaming apparatus passes through a pedicle of a vertebra in the folded mode, and the spinal reaming apparatus is converted from the folded mode to the functioning mode after the spinal reaming apparatus reaches a vertebral body of the vertebra.

According to an embodiment of the present disclosure, the spinal reaming apparatus further comprises a stressed arm, and the operated element further comprises an accommodating slot and a forcing protrusion. The stressed arm connects to the eccentric shaft and is disposed in the accommodating slot, and the forcing protrusion projects from the inner wall of the accommodating slot toward the stressed arm. When the operated element is rotated, the forcing protrusion presses the stressed arm.

According to an embodiment of the present disclosure, the spinal reaming apparatus further comprises a linkage element connected with the operated element, and the linkage element includes the accommodating slot and the forcing protrusion.

In order to achieve the above and other objectives, the present disclosure further provides a spinal reaming apparatus comprising a sleeve, two eccentric shafts, an operated element and two eccentric reaming elements. The sleeve has a first end and a second end opposing the first end. The two eccentric shafts are disposed in the sleeve. The operated element is connected to the eccentric shaft and positioned proximate to the first end of the sleeve. The two eccentric reaming elements are connected to the two eccentric shafts respectively and disposed at the second end of the sleeve. When the operated element is rotated, the operated element drives the two eccentric reaming elements to rotate relative to the sleeve by the two eccentric shafts such that the spinal reaming apparatus will switch between a folded mode and a functioning mode. Further, the combined outer diameter of two the eccentric reaming elements is substantially equal to or smaller than an outer diameter of the sleeve in the folded mode.

According to an embodiment of the present disclosure, the corresponding sides of the two eccentric reaming elements are of configurations mutually matched each other.

According to an embodiment of the present disclosure, each of the two eccentric reaming elements comprises a protrusion and a recess, which are disposed on the corresponding sides of the two eccentric reaming elements. In the folded mode, the recess of one eccentric reaming element is mutually matched with the protrusion of another eccentric reaming element.

According to an embodiment of the present disclosure, the spinal reaming apparatus further comprises two stressed arms, and the operated element further comprises an accommodating slot and two forcing protrusions. The two stressed arms connect to the two eccentric shafts respectively and are disposed in the accommodating slot. The two forcing protrusions project from the inner wall of the accommodating slot toward the two stressed arms respectively. When the operated element is rotated, the two forcing protrusions press the two stressed arms respectively.

As described above, in the embodiments of the present invention, the spinal reaming apparatus comprises a sleeve, an eccentric shaft, an operated element and an eccentric reaming element. The eccentric shaft is disposed in the sleeve. The two opposing ends of the eccentric shaft are connected to the operated element and the eccentric reaming element, respectively. When the operated element is rotated, the operated element drives the eccentric reaming element to rotate relative to the sleeve on the eccentric shaft such that the spinal reaming apparatus will switch between a folded mode and a functioning mode. Therefore, the spinal reaming apparatus is able to not only pass through an anatomically narrow structure, such as the pedicle, in the folded mode, which is smaller (safer) in terms of size, but also perform a reaming procedure in an anatomically recipient structure, such as the cancellous bone in the vertebra, in the functioning mode, which is larger in terms of size, thereby reducing the risk of a rupture, which would otherwise be caused by any large surgical instrument.

The prior art has drawbacks. For instance, an implanting channel is reamed with a bone drill or a surgical drill to increase its inner diameter to around 6.5 mm to 7 mm so as to allow the implant to reach a desired expansion destination inside a vertebra. However, the implant in the implanting channel is subjected to considerable compression. As a result, when the implant is initially expanded, either the supporting arms are subjected to overly strong forces and thus bent, leading to their deformation, or the implant tilts; for example, the implant may tilt upward or downward relative to the implanting channel rather than remaining parallel to the implanting channel. Owing to the tilting of the implant, the implant may be subjected to unequal forces when being continuously expanded; as a result, the implant may deform or fail to provide sufficient support, to the detriment of the anticipated extent of the expansion. The aforesaid problems often happen to the upper arms of the supporting arms of the implant. Therefore, if the upper arms of the supporting arms are not in direct contact with any bone tissue from the very beginning, the aforesaid problems can be addressed. In this regard, one of the advantages of reaming the implanting channel with the spinal reaming apparatus of the present disclosure is described below. The reaming procedure is performed at an implant expansion position (for example, the cancellous bone) to form an implanting channel whose inner diameter is greater than the outer diameter of the implant, such that the upper arms of the supporting arms of the implant cannot come into contact with the osteo-wall of the implanting channel; hence, as soon as it is expanded, the implant is not immediately subjected to overly strong forces but can expand a little bit so as to prevent bend-associated deformation and the implant's deviation from the planned implanting path.

BRIEF DESCRIPTION OF THE DRAWINGS

FIG. 6A is a partial enlarged schematic view of the spinal reaming apparatus shown in FIG. 1 operating in the folded mode;

FIG. 6B is a partial enlarged schematic view of the spinal reaming apparatus shown in FIG. 1 operating in the functioning mode;

FIG. 7A is a cross-sectional view of the spinal reaming apparatus shown in FIG. 6A, taken along the line A-A therein, operating in the folded mode;

FIG. 7B is a cross-sectional view of the spinal reaming apparatus shown in FIG. 6B, taken along the line A-A therein, operating in the functioning mode;

DETAILED DESCRIPTION OF THE EMBODIMENTS

The present disclosure is hereunder illustrated by preferred embodiments.

Figure 1A:
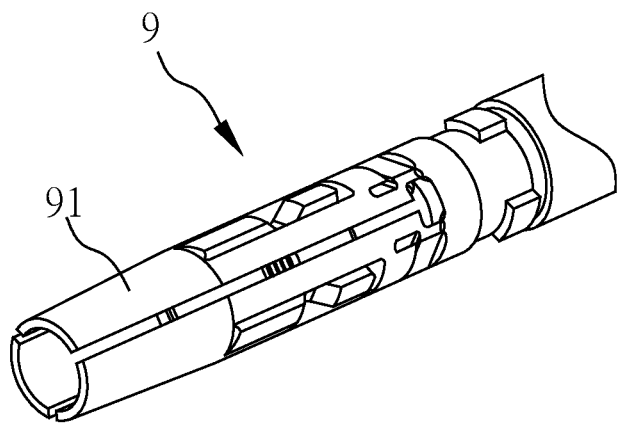
FIG. 1A and FIG. 1B (PRIOR ART) are schematic views of an implant for performing vertebrae restoration by spinal surgery.
Figure 1B:
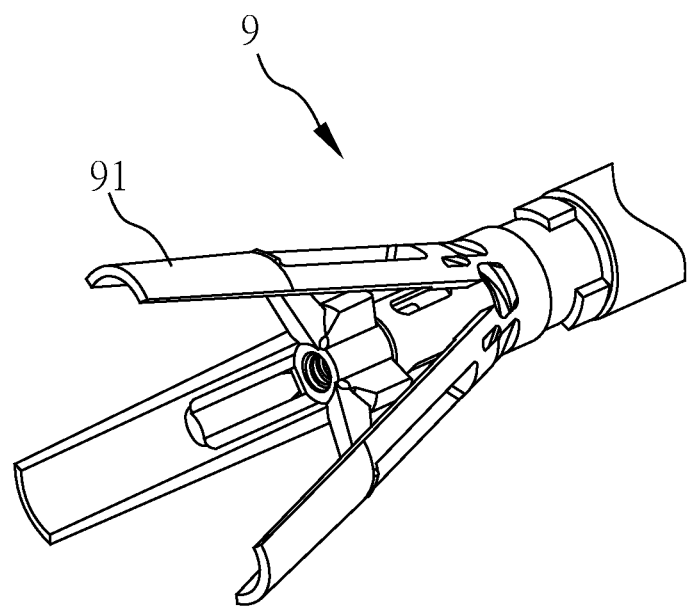

Before implanting the implant 9 (shown in FIG. 1A and FIG. 1B), a surgeon creates a hole at a planned pedicle entry point on a vertebra 8 (shown in FIG. 10A) with an awl and follows a planned surgical path to pass through a pedicle 81 to finally reach the cancellous bone in a vertebra 82, thereby forming an implanting channel 801. Afterward, the surgeon marks the implanting channel 801 and an desired expansion position with a guide wire and confirms the implanting channel 801 and the desired expansion position with a C-arm fluoroscopy X-ray (C-Arm for short). In another embodiment, a hole (at the planned pedicle entry point) can be created with a trocar. The trocar has a separable handle such that a guide wire can be inserted into its hollow casing.

For the sake of illustration, in this embodiment, the channel created with an awl and a bone drill or a surgical drill is referred to as the implanting channel 801, whereas the space created by a reaming procedure performed with a spinal reaming apparatus 1 in this embodiment is referred to as an implanting space 802. The implanting space 802 is situated in the cancellous bone at the desired expansion position or at anywhere other than a pedicle. Then, as disclosed by the prior art, the surgeon reams the implanting channel 801. Under the guidance of the guide wire, the surgeon uses a bone drill or a surgical drill of larger size (outer diameter of 6.5 mm to 7 mm, for example) or a plurality of bone drills or surgical drills of different sizes (outer diameters of 3, 4, 6.5 or 7 mm, for example) to ream the implanting channel 801. However, to prevent a rupture from happening to the pedicle 81, the maximum size of the implanting channel 801 is, even after the reaming procedure, confined to the range of 6.5 mm to 7 mm or less. In another embodiment, under the guidance of the guide wire, the surgeon operates a reamer set, which is composed of a cannula and a reamer, passed through by the guide wire, so as to ream the implanting channel 801. The advantage of the reamer set is that, upon completion of the reaming procedure, the surgeon only needs to remove the reamer and keeps the cannula in the implanting channel 801 such that the cannula will guide the manipulation of subsequent instruments, including the spinal reaming apparatus 1 and any tool for use in implanting the implant 9.

Afterward, the surgeon uses the spinal reaming apparatus 1 in this embodiment to further perform a reaming procedure on the cancellous bone in the vertebra 82 with a view to forming the implanting space 802, whose inner diameter is greater than the outer diameter of the implant 9. The details of the structures of the spinal reaming apparatus 1 are described below, and the reaming procedure performed with the spinal reaming apparatus 1 is explained thereafter.

Figure 2:
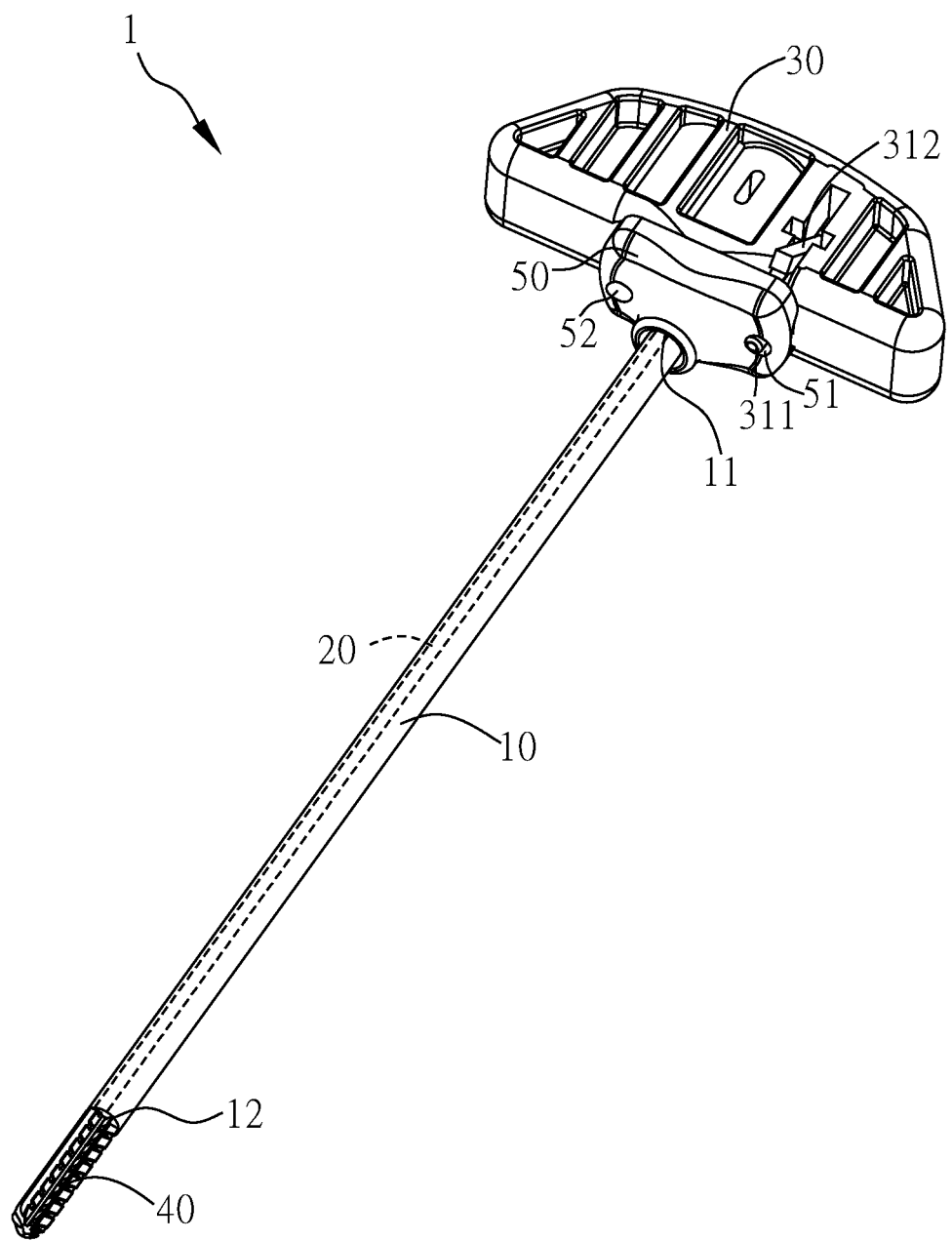
FIG. 2 is a perspective view of a spinal reaming apparatus according to an embodiment of the present disclosure.
Figure 3:
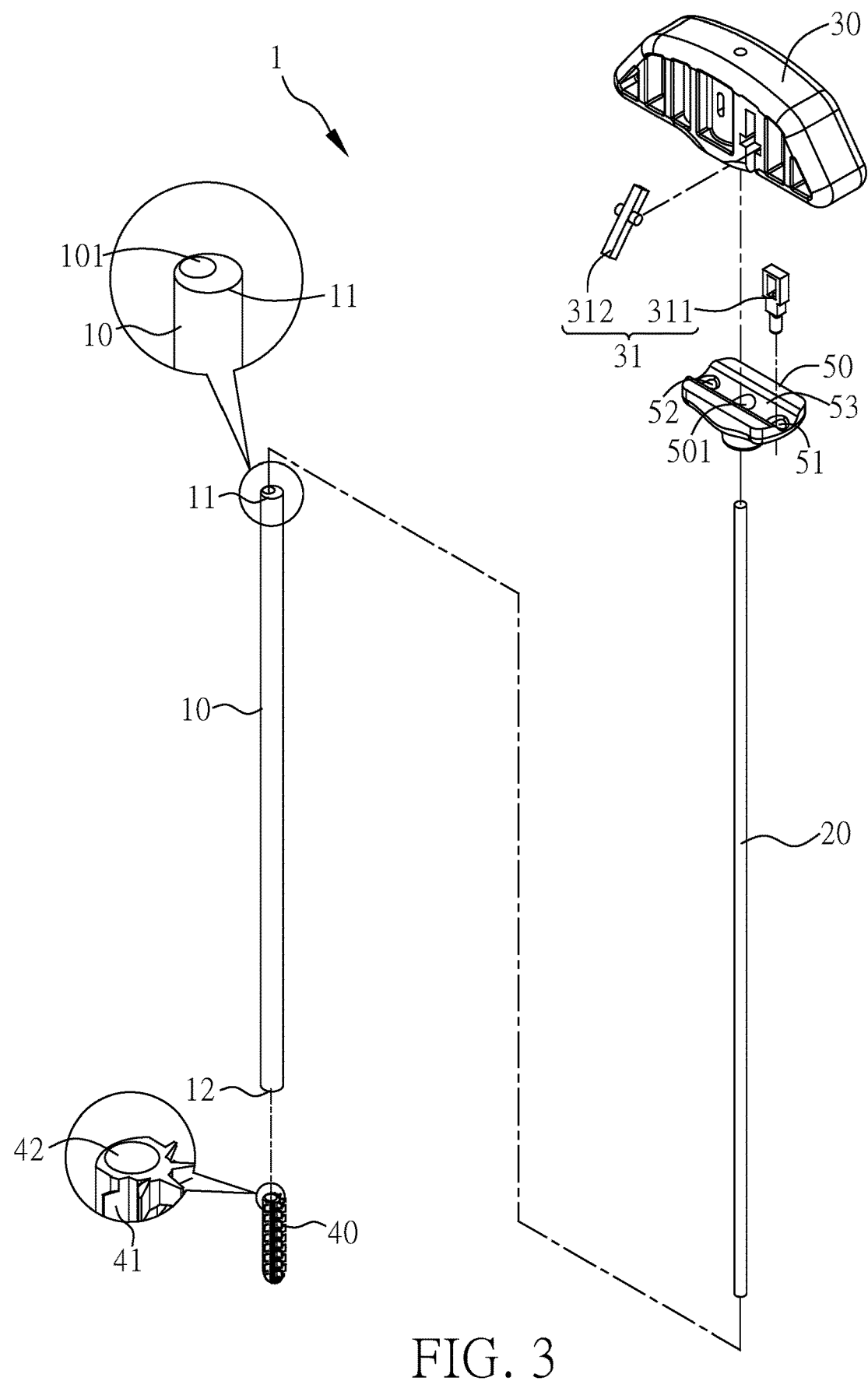
FIG. 3 is an exploded view of the spinal reaming apparatus shown in FIG. 2.

FIG. 2 is a perspective view of a spinal reaming apparatus according to an embodiment of the present disclosure. FIG. 3 is an exploded view of the spinal reaming apparatus shown in FIG. 2. Referring to FIG. 2 and FIG. 3, in this embodiment, the spinal reaming apparatus 1 comprises a sleeve 10, an eccentric shaft 20, an operated element 30 and an eccentric reaming element 40. The eccentric shaft 20 is passed through and accommodated in the sleeve 10. One end of the eccentric shaft 20 is connected to the operated element 30, and the other end of the eccentric shaft 20 is connected to the eccentric reaming element 40. For clarity, one end (proximate to the operated element 30) of the sleeve 10 is referred to as the first end 11 hereinafter, and the other end (proximate to the eccentric reaming element 40) is referred to as the second end 12 hereinafter. In this embodiment, the sleeve 10 has a first end 11 and a second end 12, and the second end 12 is opposite to the first end 11. The operated element 30 is proximate to the first end 11 of the sleeve 10, and the eccentric reaming element 40 is disposed at the second end 12 of the sleeve 10.

Figure 4:
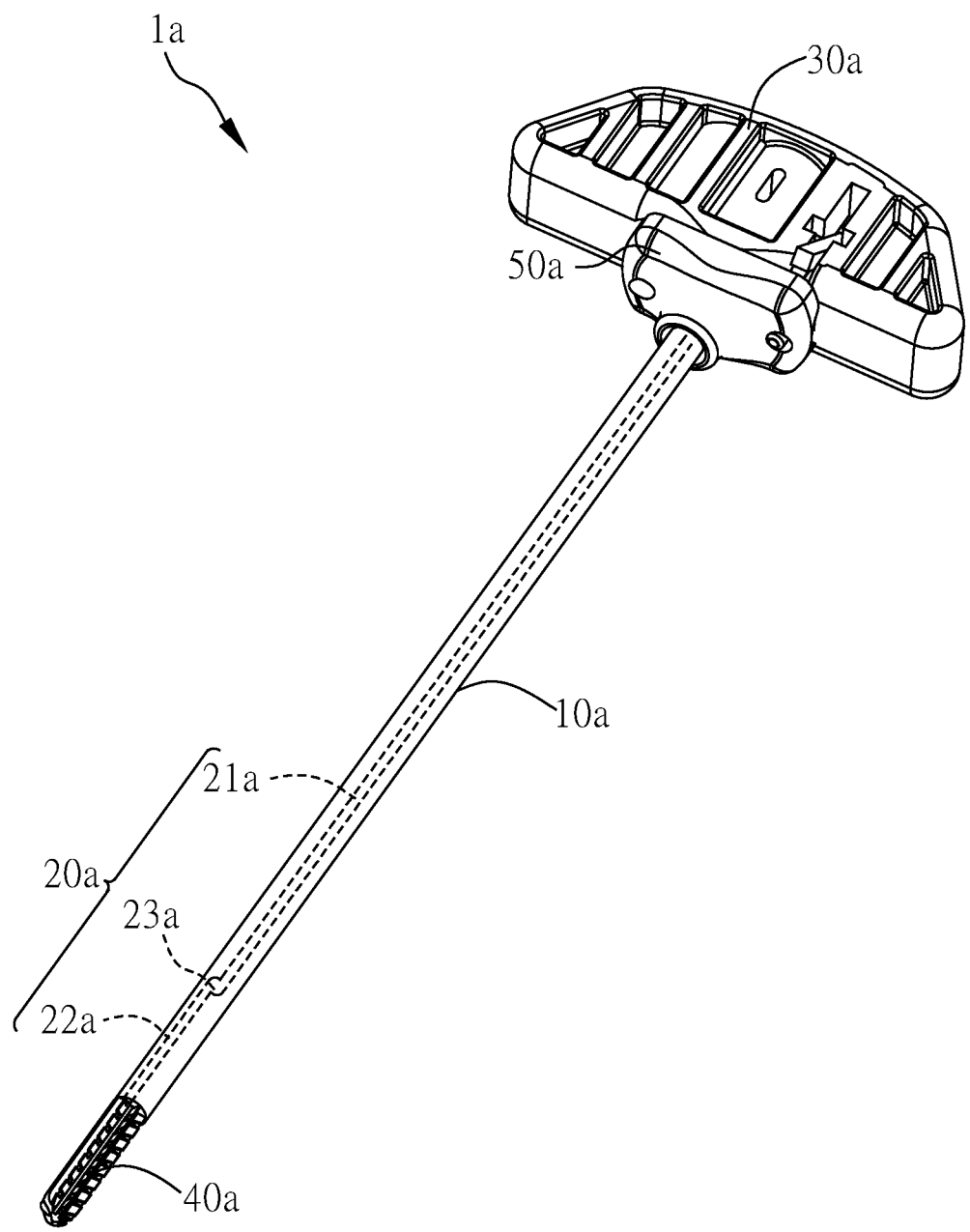
FIG. 4 is a schematic view of an eccentric reaming element according to another embodiment of the present disclosure.

In this embodiment, the eccentric shaft 20 is slender and cylindrical, and the eccentric shaft 20 is passed through the sleeve 10 eccentrically and accommodated therein. Hence, the sleeve 10 is not concentric with the eccentric shaft 20, nor do the projection of the axial center of the sleeve 10 and the projection of the axial center of the eccentric shaft 20 overlap. In another embodiment, the eccentric shaft 20a could be any other shape or comprise any other component, as shown in FIG. 4. FIG. 4 is a schematic view of the eccentric reaming element according to another embodiment of the present disclosure. In this embodiment, the eccentric shaft 20a comprises a central axial portion 21a, an eccentric shaft portion 22a and a linking axial portion 23a. The central axial portion 21a is not necessarily eccentric relative to the sleeve 10a; however, the eccentric shaft portion 22a must be disposed in the sleeve 10a and positioned proximate to the eccentric reaming element 40a, whereas the central axial portion 21a and the eccentric shaft portion 22a are connected by the linking axial portion 23a, thereby achieving the same functioning mode. In another embodiment, the central axial portion 21a and the eccentric shaft portion 22a are connected by a gear train, but the present disclosure is not limited thereto.

In this embodiment, the spinal reaming apparatus 1 further comprises a gripping element 50 disposed at the first end 11 of the sleeve 10 and between the sleeve 10 and the operated element 30. Specifically speaking, in this embodiment, the gripping element 50 is fixedly connected to the sleeve 10, whereas the eccentric shaft 20 passes through an assembly hole 501 of the gripping element 50 to thereby fixedly connect to the operated element 30. The sleeve 10 has a hollow channel 101 (shown in FIG. 3). The eccentric shaft 20 is disposed in the hollow channel 101 and is rotatable. The eccentric shaft 20 is also rotatable in the assembly hole 501. In practice, the surgeon grips the gripping element 50 with two fingers to stabilize the spinal reaming apparatus 1 and then rotates the operated element 30 with the other hand to exert a force on the operated element 30. When the surgeon rotates the operated element 30, the eccentric shaft 20 connected to the operated element 30 can be rotated within the gripping element 50 and the sleeve 10, but the gripping element 50 and the sleeve 10 are stationary.

Figure 5:
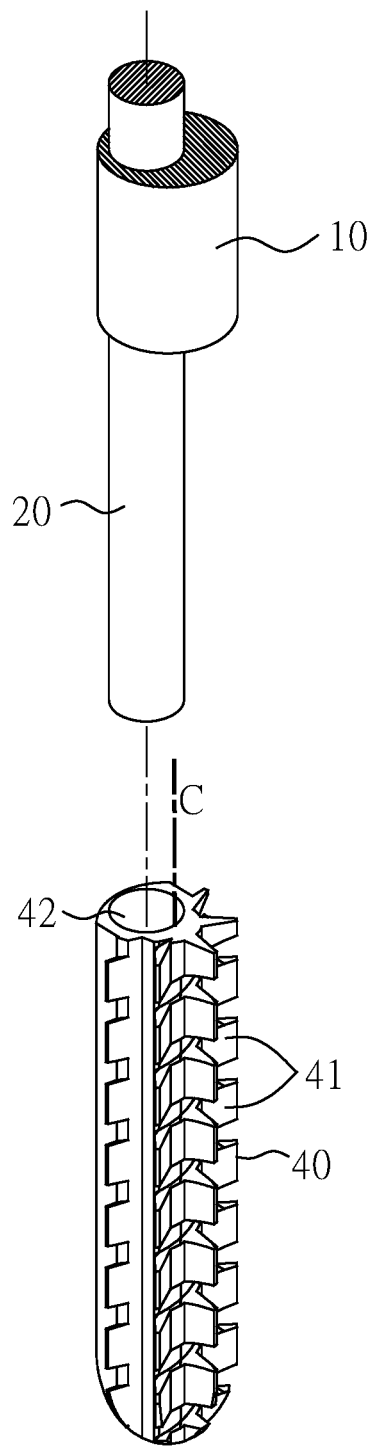
FIG. 5 is an enlarged exploded view of an eccentric shaft and the eccentric reaming element shown in FIG. 2.

The other end of the eccentric shaft 20 is connected to the eccentric reaming element 40. Therefore, when the operated element 30 is rotated, the operated element 30 drives the eccentric reaming element 40 to rotate on the eccentric shaft 20 relative to the sleeve 10. FIG. 5 is an enlarged exploded view of an eccentric shaft and the eccentric reaming element shown in FIG. 2. Referring to FIG. 5, when the eccentric reaming element 40 is rotated with the eccentric shaft 20 as a pivot, an imaginary circular path is depicted. Since the position at which the eccentric shaft 20 connects to the eccentric reaming element 40 is not aligned with the central axis C but is closer to the outside of the central axis C, a radius R2 of the depicted circular path formed by the rotation of the eccentric reaming element 40 is greater than a radius R1 of the sleeve 10 (shown in FIG. 7A and FIG. 7B). The eccentric reaming element 40 protrudes from the sleeve 10 gradually and then retreats into the sleeve 10 gradually in the course of one revolution about the eccentric shaft 20. With the eccentric reaming element 40 protruding from the sleeve 10, when the spinal reaming apparatus 1 is rotated a complete turn, a larger circular path is formed by the eccentric reaming element 40, and thereby the vertebra is cut in such a manner to form an implanting space 802 of a greater inner diameter. After the eccentric reaming element 40 has retreated into the sleeve 10, the eccentric reaming element 40 and the sleeve 10 are aligned and thus their circular paths overlap. In this embodiment, the former occurs in the functioning mode of the spinal reaming apparatus 1, whereas the latter occurs in the folded mode of the spinal reaming apparatus 1, allowing the surgeon to switch between the folded mode and the functioning mode of the spinal reaming apparatus 1 by rotating the operated element 30.

In this embodiment, the eccentric reaming element 40 is substantially flush with the sleeve 10 in the folded mode and protrudes from the sleeve 10 in the functioning mode, as shown in FIG. 6A and FIG. 6B. FIG. 6A is a partial enlarged schematic view of the spinal reaming apparatus shown in FIG. 1 operating in the folded mode. FIG. 6B is a partial enlarged schematic view of the spinal reaming apparatus shown in FIG. 1 operating in the functioning mode. FIG. 7A is a cross-sectional view of the spinal reaming apparatus shown in FIG. 6A, taken along the line A-A therein, operating in the folded mode. FIG. 7B is a cross-sectional view of the spinal reaming apparatus shown in FIG. 6B, taken along the line A-A therein, operating in the functioning mode. Referring to FIG. 6A and FIG. 7A, in this embodiment, the sleeve 10 is substantially flush with the eccentric reaming element 40 because the outer diameter of the sleeve 10 is substantially the same as the outer diameter of the eccentric reaming element 40, such that the outer surface of the sleeve 10 and the outer surface of the eccentric reaming element 40 do not differ in height at their junction, allowing the spinal reaming apparatus 1 to be consistent in terms of size along the direction from the sleeve 10 to the eccentric reaming element 40 (as shown in FIG. 6A), but the other embodiments of the present disclosure are not limited thereto. In a variant embodiment of the present disclosure, the sleeve 10 differs from the eccentric reaming element 40 in terms of size and/or shape. For instance, the outer diameter of the sleeve 10 is greater than or less than the outer diameter of the eccentric reaming element 40. Although the sleeve 10 and the eccentric reaming element 40 differ in terms of outer diameter and are not flush with each other in height, the spinal reaming apparatus 1 will function well, provided that the size of the eccentric reaming element 40 matches that of the position of connection between the eccentric reaming element 40 and the eccentric shaft 20 such that the eccentric reaming element 40 attains a larger rotation radius in the functioning mode than in the folded mode (as shown in FIG. 7A).

In this embodiment, the eccentric reaming element 40 is a cylinder covered with a plurality of cutting portions 41, and the cutting portions 41 are disposed on the outer surface of the eccentric reaming element 40. The outer diameter of the eccentric reaming element 40 is defined as the outer diameter of an imaginary cylinder formed by connecting the outermost edges of the cutting portions 41, and the outer diameter of the eccentric reaming element 40 is substantially equal to the outer diameter of the sleeve 10. In this embodiment, the eccentric reaming element 40 has the cutting portions 41 and a connecting portion 42. The cutting portions 41 are disposed on the outer surface and on one side of the eccentric reaming element 40. The connecting portion 42 is disposed on the other side of the eccentric reaming element 40. In this embodiment, the connecting portion 42 has a hole whereby the eccentric shaft 20 can be inserted into the connecting portion 42. The cutting portions 41 are not necessarily present on the outer surface of the connecting portion 42; however, the cutting portions 41 on the eccentric reaming element 40 may be dispensed with in order to reserve sufficient space for accommodating the eccentric shaft 20.

Referring to FIG. 6B and FIG. 7B, when the operated element 30 is rotated, the eccentric shaft 20 is also rotated within the sleeve 10, and the eccentric shaft 20 drives the eccentric reaming element 40 to rotate relative to the sleeve 10. The eccentric shaft 20 is eccentrically disposed in the sleeve 10 and connected to a non-central point of the eccentric reaming element 40; hence, the eccentric reaming element 40 rotates eccentrically and relative to the sleeve 10 with the eccentric shaft 20 as a pivot such that the cutting portions 41 will protrude from the sleeve 10 gradually. In this embodiment, the cutting portions 41 are dentate and sharpened. In another embodiment, the cutting portions 41 can be spiral, sharpened or fluted and thus adapted to scrape off tissue from the vertebra 82.

In this embodiment, the eccentric reaming element 40 and the sleeve 10 have the same radius, i.e., a first radius R1. Preferably, the first radius R1 is between 3 mm and 3.2 mm. The eccentric reaming element 40 is rotated to form a circular path, i.e., a circle defined by the first radius R1, which matches the circumference of the sleeve 10, in response to a complete turn made by the spinal reaming apparatus 1 in the folded mode.

After the spinal reaming apparatus 1 has switched to the functioning mode as shown in FIG. 6B and FIG. 7B, the spinal reaming apparatus 1 makes a complete turn, and a circular trajectory T formed by the eccentric reaming element 40, that is, the circular trajectory T formed by the outermost edges of the cutting portions 41, has a second radius R2. The second radius R2 is greater than the first radius R1. The second radius R2 is between 4 mm and 7 mm, preferably between 6 mm and 7 mm. Since the eccentric reaming element 40 protrudes from the sleeve 10 in the functioning mode, the radius (the second radius R2) of the circular trajectory T formed by the eccentric reaming element 40 is greater than the radius (the first radius R1) of the eccentric reaming element 40 itself. For instance, the first radius R1 is 3 mm and the height of the cutting portions 41 are 1 mm, so the length by which the eccentric reaming element 40 protrudes from the sleeve 10 is around 1 mm (exclusive of the thickness of the wall of the sleeve 10) in the functioning mode. Therefore, when the spinal reaming apparatus 1 is rotated, the radius (the second radius R2) of the circular trajectory T formed by the eccentric reaming element 40 is around 4 mm.

Figure 8A:
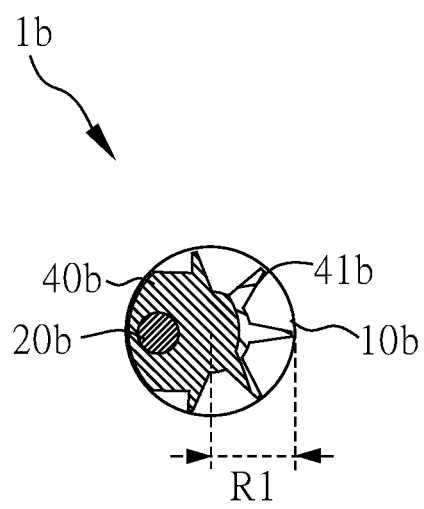
FIG. 8A and FIG. 8B are cross-sectional views of the eccentric reaming element according to another embodiment of the present disclosure.
Figure 8B:
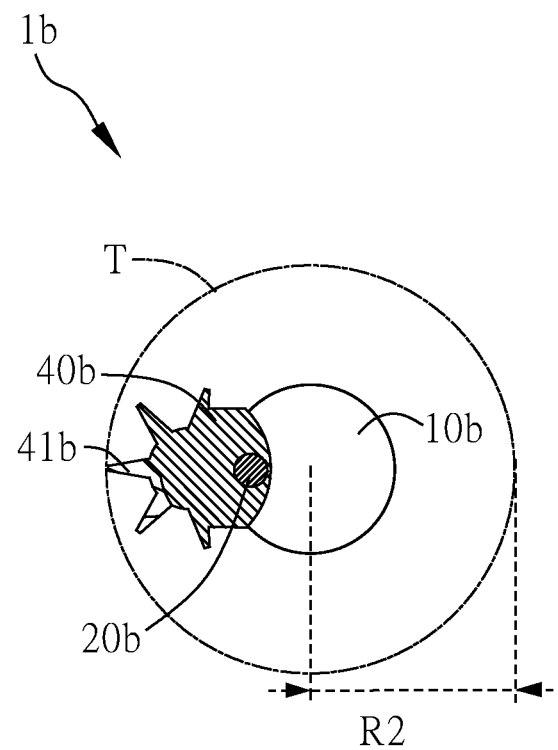

In another embodiment of the present disclosure, the second radius R2 is adjusted according to the location of the connection between the eccentric shaft 20 and the eccentric reaming element 40, the level of eccentricity of the eccentric shaft 20 within the sleeve 10, and the size of the eccentric shaft 20. FIG. 8A and FIG. 8B are cross-sectional views of the eccentric reaming element according to another embodiment of the present disclosure. Referring to FIG. 8A and FIG. 8B, in this embodiment, the eccentric reaming element 40b and the sleeve 10b are of the same radius, i.e., the first radius R1, wherein the first radius R1 is 3 mm, as shown in FIG. 3A. However, in this embodiment, with the eccentric shaft 20b being of a small radius of 0.75 mm, being highly eccentric within the sleeve 10b, and being connected to the outermost part of the eccentric reaming element 40b, the eccentric distance between the sleeve 10b and the eccentric shaft 20b is greater than its counterpart in the preceding embodiment; the second radius R2 increases to 6.9 mm while in the functioning mode, as shown in FIG. 8B. Persons skilled in the art will understand that the eccentric distance can be adjusted according to the aforesaid concept so as to attain the first radius R1 and the second radius R2.

In the preceding embodiment, the eccentric reaming element 40 is designed to rotate by 180 degrees such that the second radius R2 can be maximized to allow the spinal reaming apparatus 1 to switch to the functioning mode. Similarly, the eccentric reaming element 40 is further rotated by 180 degrees such that the spinal reaming apparatus 1 returns to the folded mode, but the present disclosure is not limited thereto. In another embodiment, the eccentric reaming element 40 is rotated by 90 degrees, 120 degrees, 150 degrees or any specific number of degrees such that the spinal reaming apparatus 1 switches to the functioning mode, and the variation in the degrees of rotation of the eccentric reaming element 40 even results in variation in the extent of protrusion of the eccentric reaming element 40 such that the surgeon can choose the degree of rotation of the eccentric reaming element 40 to meet various reaming requirements.

Figure 9A:
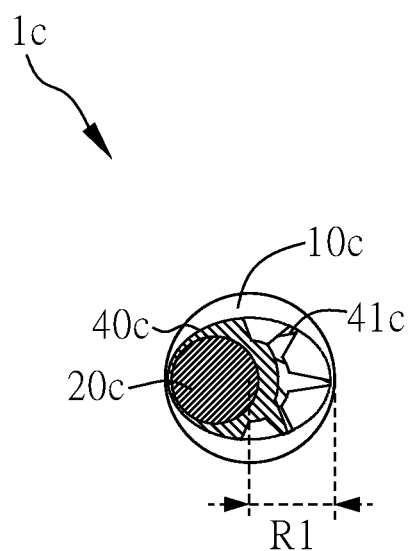
FIG. 9A and FIG. 9B are cross-sectional views of the eccentric reaming element according to yet another embodiment of the present disclosure.
Figure 9B:
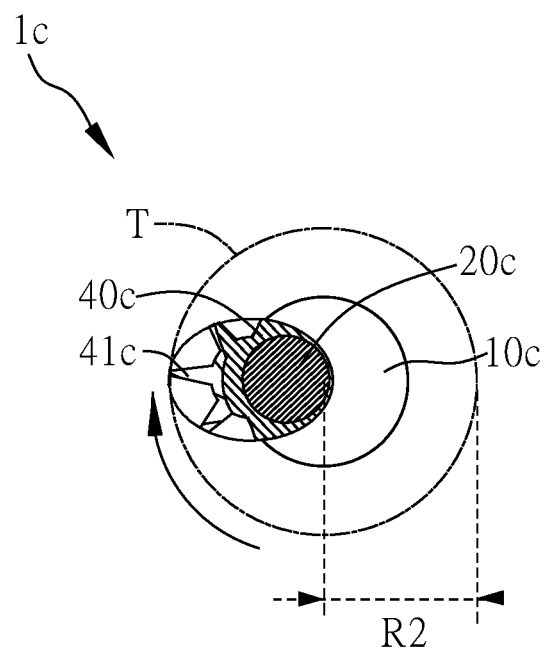

FIG. 9A and FIG. 9B are cross-sectional views of the eccentric reaming element according to yet another embodiment of the present disclosure. The spinal reaming apparatus 1c shown in FIG. 9A is operating in the folded mode. The spinal reaming apparatus 1c shown in FIG. 9B is operating in the functioning mode. In this embodiment, the eccentric reaming element 40c has an elliptical cross section. The dashed lines in FIG. 9A and FIG. 9B depict the ellipses formed by connecting the outer edges of the cutting portions 41c, respectively. The eccentric shaft 20c is connected to one of the foci of the ellipse (as shown in the cross-sectional views of FIG. 9A and FIG. 9B). Similarly, the aforesaid configuration enables the eccentric reaming element 40c to attain a larger rotation radius in the functioning mode (i.e., the second radius R2 shown in FIG. 9B).

Figure 15A:
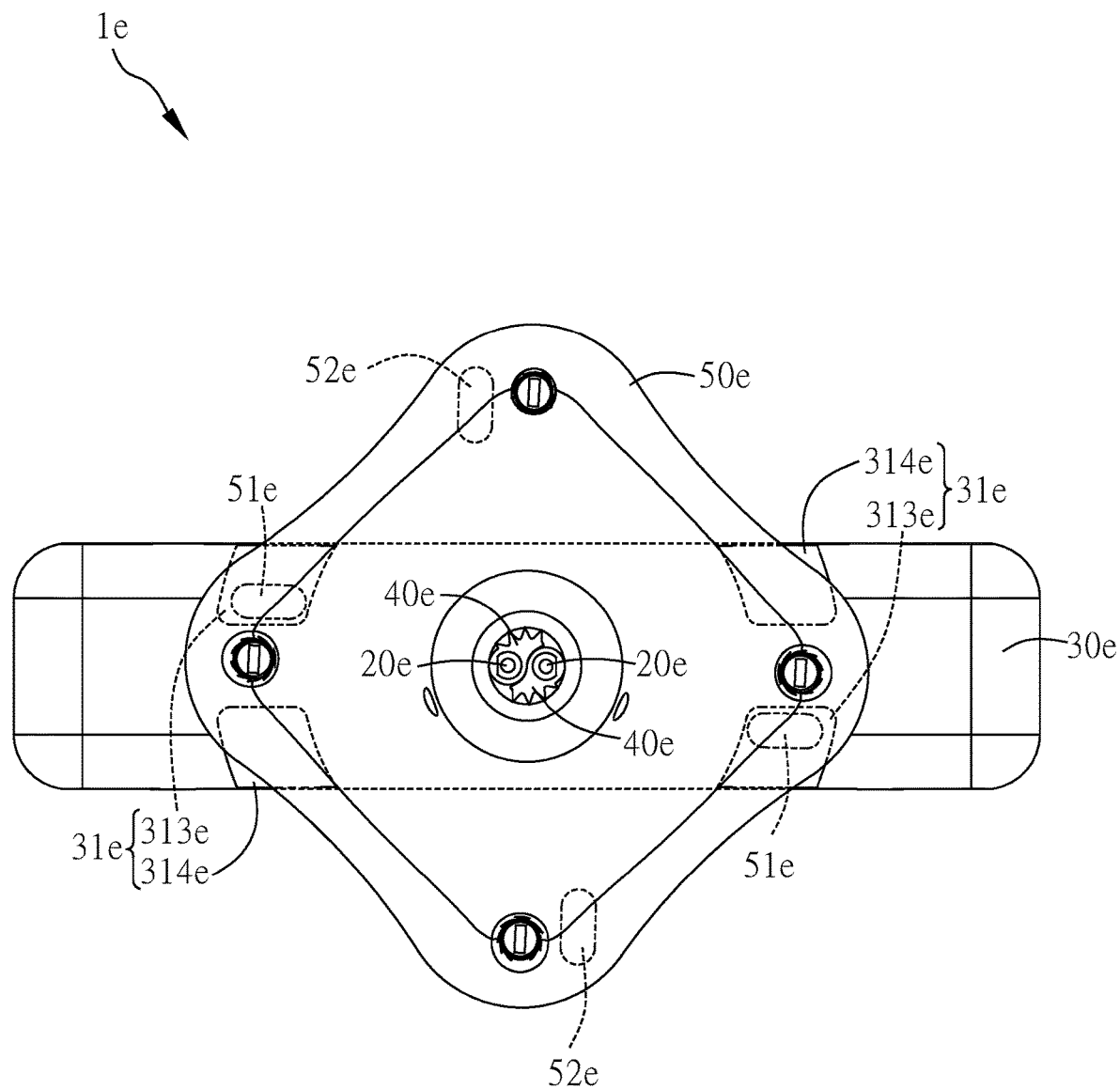
FIG. 15A is a bottom view of the spinal reaming apparatus shown in FIG. 12 operating in the folded mode.

Preferably, as shown in FIG. 2 and FIG. 3, the operated element 30 comprises a first positioning portion 31, whereas the gripping element 50 comprises two second positioning portions 51, 52. The first positioning portion 31 engages with the second positioning portions 51, 52. For instance, in this embodiment, the first positioning portion 31 has a protrusion. Preferably, the first positioning portion 31 comprises a pin 311 (protrusion) and a lever 312, whereas, correspondingly, the two second positioning portions 51, 52 are each a recess. Specifically speaking, the second positioning portions 51, 52 are recesses disposed on a surface of the gripping element 50 (the surface of the gripping element 50 faces the operated element 30) or holes passing through the gripping element 50. This embodiment is exemplified by holes passing through the gripping element 50. In another embodiment, the first positioning portion 31 is a recess, whereas the second positioning portions 51, 52 are protrusions (as shown in FIG. 15A; the details are described below) or any structure corresponding in contour to the recess, but the present disclosure is not limited thereto. The present disclosure is not restrictive of the number of the first positioning portions and the number of the second positioning portions.

The two second positioning portions 51, 52 are opposite each other such that an included angle of 180 degrees is formed between the second positioning portion 51 and the second positioning portion 52. Therefore, every time the operated element 30 is rotated by 180 degrees, not only does the spinal reaming apparatus 1 switch between the folded mode and the functioning mode, but the first positioning portion 31 also engages with one of the two second positioning portions 51, 52 (i.e., the second positioning portion 51 or the second positioning portion 52) to thereby keep the spinal reaming apparatus 1 in the folded mode or in the functioning mode. For instance, the spinal reaming apparatus 1 is kept in the folded mode when the first positioning portion 31 engages with the second positioning portion 51 (when the pin 311 is inserted into the second positioning portion 51), whereas the spinal reaming apparatus 1 is kept in the functioning mode when the first positioning portion 31 engages with the second positioning portion 52. In another embodiment, the operated element 30 has a fastening unit, and the position of the operated element 30 relative to the gripping element 50 is fixed through the fastening unit, but the present disclosure is not limited thereto.

In this embodiment, the two second positioning portions 51, 52 are disposed in a limiting portion 53, and the limiting portion 53 is a groove. After the first positioning portion 31 has been rotated and admitted into the limiting portion 53, the surgeon has to exert a stronger force on the first positioning portion 31 in order to rotate and remove the first positioning portion 31 from the limiting portion 53 and thereby to switch the spinal reaming apparatus 1 between the folded mode and the functioning mode. In this regard, the limiting portion 53 enhances the ease of use when the first positioning portion 31 is a hemispherical protrusion instead of a pin.

In another embodiment, the gripping element 50 further comprises a guide groove serving as a guide for the path of the movement of the pin 311 of the first positioning portion 31. The two second positioning portions 51, 52 are disposed at the two opposing ends of the guide groove, respectively. When the operated element 30 is rotated, the pin 311 of the first positioning portion 31 moves along the guide groove. The first positioning portion 31 moves from the second positioning portion 51 to the second positioning portion 52 such that the spinal reaming apparatus 1 switches to the functioning mode. The first positioning portion 31 moves from the second positioning portion 52 to the second positioning portion 51 such that the spinal reaming apparatus 1 returns to the folded mode.

The spinal reaming apparatus 1 can keep operating in the folded mode or in the functioning mode to enable the surgeon to perform the reaming procedure on the vertebra 82 easily. FIG. 10A through FIG. 10E are schematic views of how to manipulate the spinal reaming apparatus shown in FIG. 1. FIG. 10A through FIG. 10E illustrate how to perform the spinal reaming apparatus 1 during the reaming procedure and depict the engagement of the first positioning portion 31 and the second positioning portions 51, 52. For clarity, FIG. 10A through FIG. 10E omit any other auxiliary surgical instruments, such as a cannula or a guide wire. For instance, while performing the reaming procedure with the trocar, the surgeon inserts the spinal reaming apparatus 1 into a cannula such that, under the guidance of the cannula, the spinal reaming apparatus 1 reaches the desired reaming position before the reaming procedure begins.

Figure 10A:
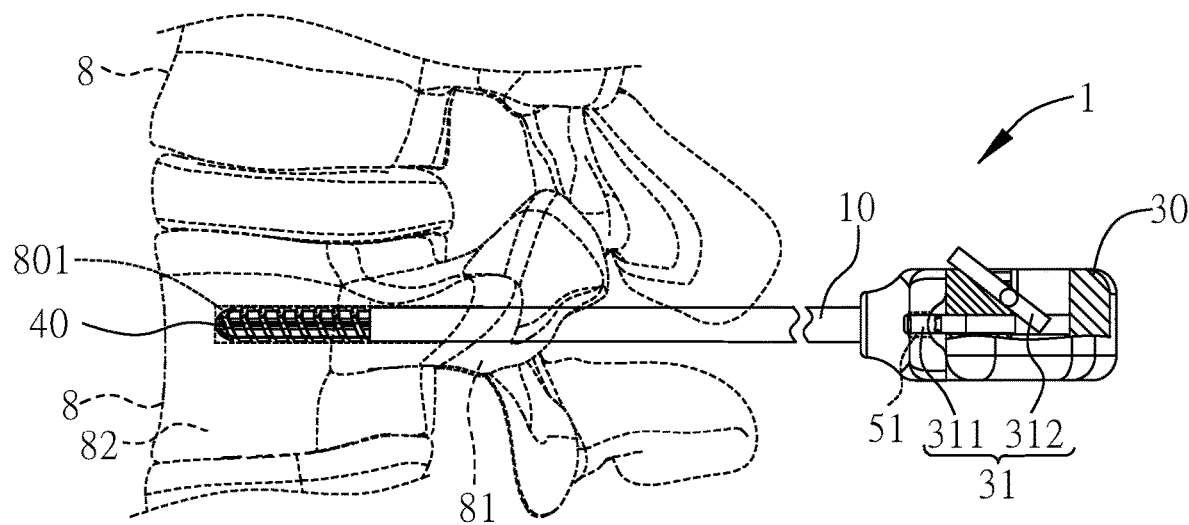
FIG. 10A through FIG. 10E are schematic views of how to manipulate the spinal reaming apparatus shown in FIG. 1.

Before using the spinal reaming apparatus 1 of this embodiment, the surgeon creates a hole as an implanting point of entry on the vertebra 8 with instruments, such as an awl, a probe, a bone drill and a surgical drill, consecutively, so as to form an implanting channel 801 which passes through the pedicle 81 and reaches the cancellous bone in the vertebra 82. Afterward, the surgeon places the spinal reaming apparatus 1 in the implanting channel 801 in the folded mode such that the spinal reaming apparatus 1 passes through the pedicle 81 and reaches the desired expansion position to be expanded by the implant 9, as shown in FIG. 10A. For safety, a bone drill or a surgical drill usually has an outer diameter of less than around 6.5 mm to 7 mm, and in consequence, the implanting channel 801 thus formed has an inner diameter of less than around 6.5 mm to 7 mm. In this embodiment, the radius (the first radius R1) of the eccentric reaming element 40 is between 3 mm and 3.2 mm, and thus the overall outer diameter of the eccentric reaming element 40 is between 6 mm and 6.4 mm; that is, the overall outer diameter of the eccentric reaming element 40 is less than the inner diameter (6.5 mm) of the implanting channel 801. Therefore, the eccentric reaming element 40 can pass through the pedicle 81 and enter the vertebra 82.

Figure 10B:
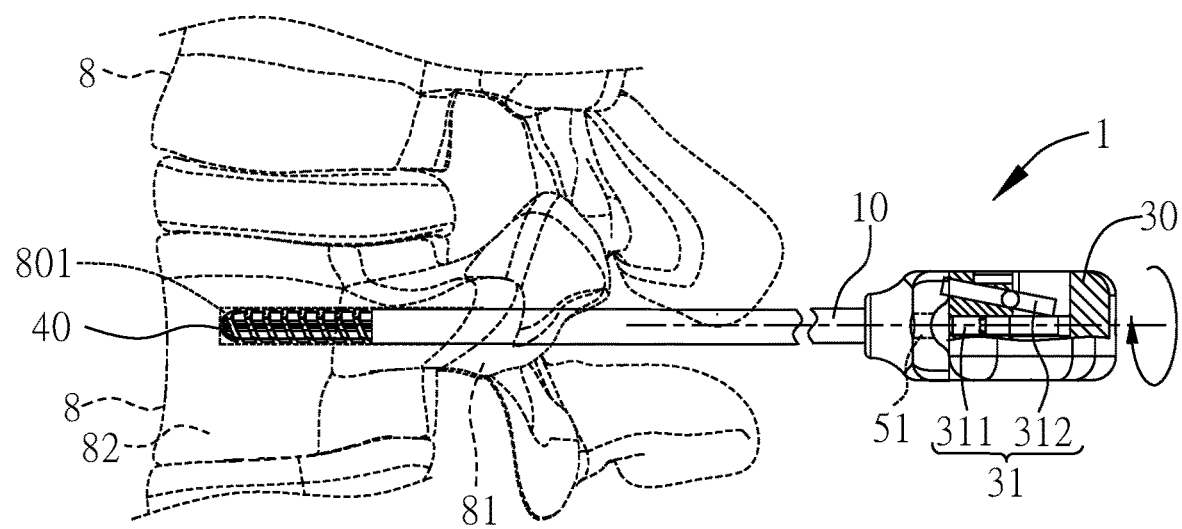
Figure 10C:
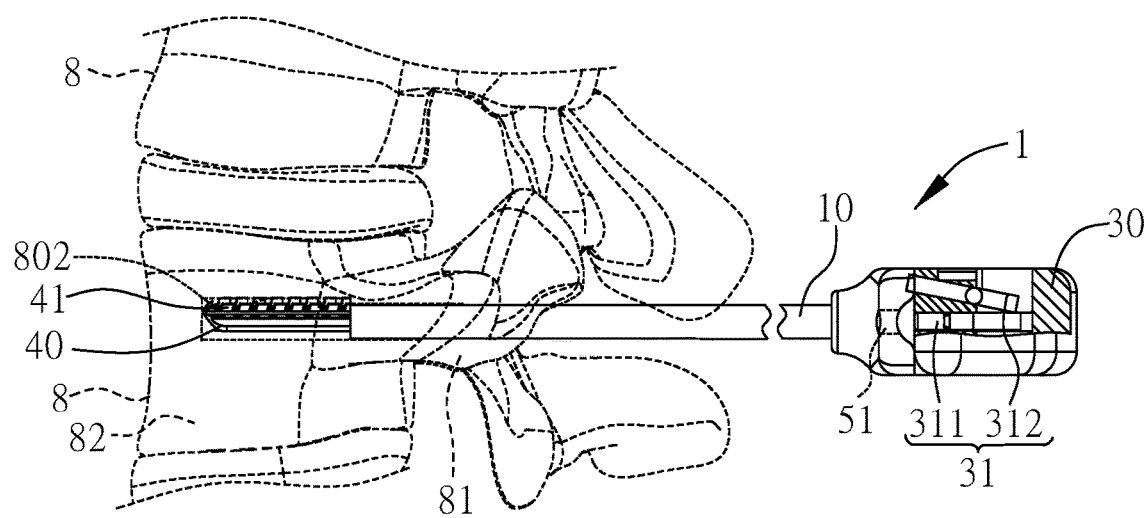
Figure 10D:
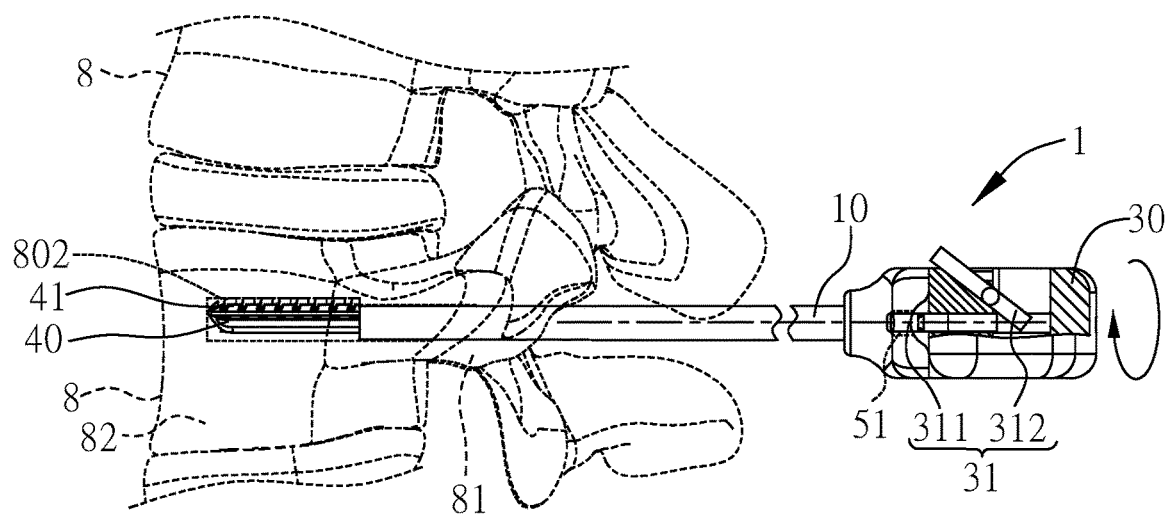

Afterward, the surgeon switches the spinal reaming apparatus 1 to the functioning mode. Specifically speaking, the surgeon presses the lever 312 in the direction toward the interior of the operated element 30 (as shown in FIG. 10A) such that the pin 311 is lifted and thus separated from the second positioning portion 51 (as shown in FIG. 10B). Afterward, the surgeon fixes the gripping element 50 in place with one hand and rotates the operated element 30 by 180 degrees with the other hand. At this moment, the first positioning portion 31 is rotated by 180 degrees and thus moves from the second positioning portion 51 to the second positioning portion 52 (as shown in FIG. 10C). At this moment, the eccentric shaft 20 drives the eccentric reaming element 40 to rotate such that the cutting portions 41 of the eccentric reaming element 40 protrude from the sleeve 10. FIG. 10A and FIG. 10B are viewed from the vicinity of the second positioning portion 51, whereas FIG. 10C and FIG. 10D are viewed from the vicinity of the second positioning portion 52. When the pin 311 moves to the second positioning portion 52, the lever 312 is pushed in the direction away from the operated element 30; that is, the lever 312 is pushed upward, starting from FIG. 10C and ending in FIG. 10D, so as to insert the pin 311 into the second positioning portion 52 such that the first positioning portion 31 engages with the second positioning portion 52, thereby keeping the spinal reaming apparatus 1 in the functioning mode, as shown in FIG. 10D. Therefore, in this embodiment, it is only when the spinal reaming apparatus 1 enters the vertebra 82 of the vertebra 8 that the spinal reaming apparatus 1 switches to the functioning mode. Patients receive this surgery because the tissue inside the vertebra 82 is degraded or injured and thus fragile or porous; hence, the manual rotation of the operated element 30 to make the eccentric reaming element 40 to rotate and protrude from the sleeve 10 might be confronted with resistance, but the rotation is still feasible.

Figure 10E:
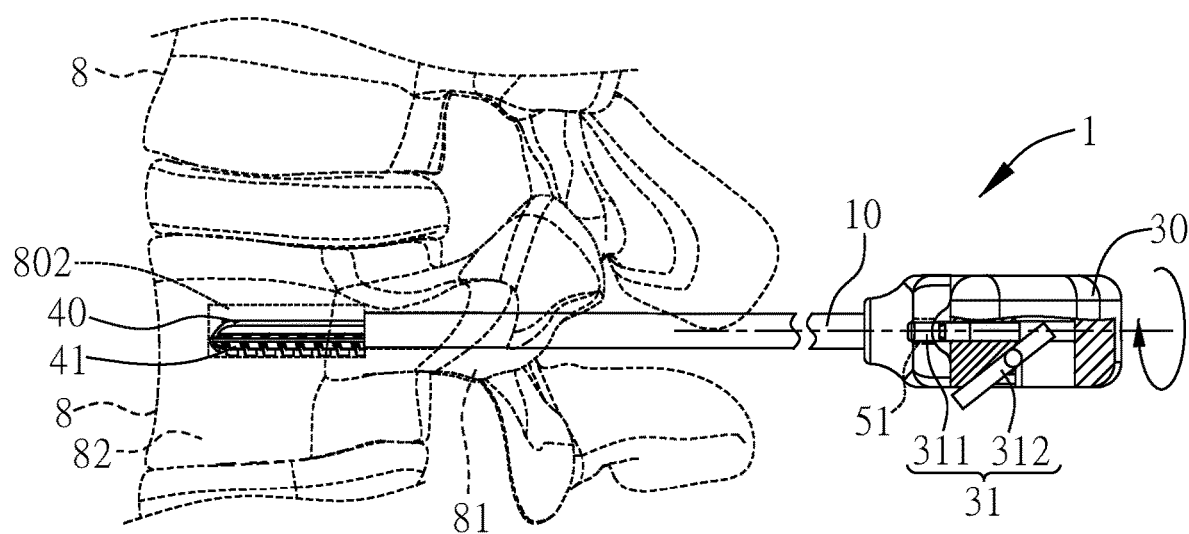

Finally, the entirety of the spinal reaming apparatus 1 in the functioning mode is rotated. Since the operated element 30 and the gripping element 50 engage with each other through the first positioning portion 31 and the second positioning portion 52, the surgeon only needs to grip and rotate the operated element 30 to cause the entirety of the spinal reaming apparatus 1 to be rotated. As soon as the spinal reaming apparatus 1 rotates in its entirety, the cutting portions 41 protruding from the sleeve 10 scrape off tissue from the vertebra 82 and thereby ream the implanting channel 801, thereby forming the implanting space 802 of a greater outer diameter, as shown in FIG. 10E. In this embodiment, it is only when the spinal reaming apparatus 1 has entered the vertebra 82 that the spinal reaming apparatus 1 is switched to the functioning mode to perform the reaming procedure, and thus the spinal reaming apparatus 1 not only prevents any rupture caused by passing a large instrument through the pedicle 81 but also performs the reaming procedure at the desired expanded position intended for the implant 9, thereby reducing surgical risks.

An inner diameter of the implanting channel 801 formed by a bone drill and a surgical drill is around 6.5 mm. In this embodiment, the length by which the eccentric reaming element 40 protrudes from the sleeve 10 is 1 mm (the second radius R2 is 4 mm), and thus the spinal reaming apparatus 1 increases the inner diameter of the implanting channel 801 formed by the awl by 1 mm, such that the diameter of the implanting space 802 (in the vertebra 82) is between 8 mm and 8.5 mm and preferably greater than the outer diameter of the implant 9. Afterward, the implant 9 having an outer diameter of 8 mm is delivered to the implanting space 802 in the vertebra 82 to provide a tiny amount of initial expansion of the space for the implant 9 and especially to provide an initial expansion space for the upper arms of the supporting arms 91 (due to gravity, the lower arms of the supporting arms 91 of the implant 9 are still in direct contact with bone tissue such that surplus space is found above the upper arms of the supporting arms 91). Therefore, the upper arms of the supporting arms 91 of the implant 9 expand outward slightly and then interfere with the inner wall of the vertebra 82 to thereby avoid providing extra space, facilitate performance, and even reduce the chance that the implant 9 will deform or deviate under unequal forces and thereby fail to provide sufficient support.

In another embodiment of the present disclosure, the spinal reaming apparatus 1 is also for use in removing tissue and thus applicable to discectomy, for example, for removing the nucleus pulposus of an intervertebral disc. The surgeon passes the trocar or an endoscope through the annulus fibrosis and then passes the spinal reaming apparatus 1 (in the folded mode) through the cannula or the endoscope's sleeve to reach the nucleus pulposus. Afterward, the surgeon switches the spinal reaming apparatus 1 to the functioning mode and uses the eccentric reaming element 40 to cut the nucleus pulposus, thereby to achieve the desired therapy. The present disclosure is not restrictive of the removal of related tissue of the spinal column; hence, the present disclosure will achieve its intended objectives, provided that the desired therapy is achieved by a means of reaming and cutting.

Figure 11A:
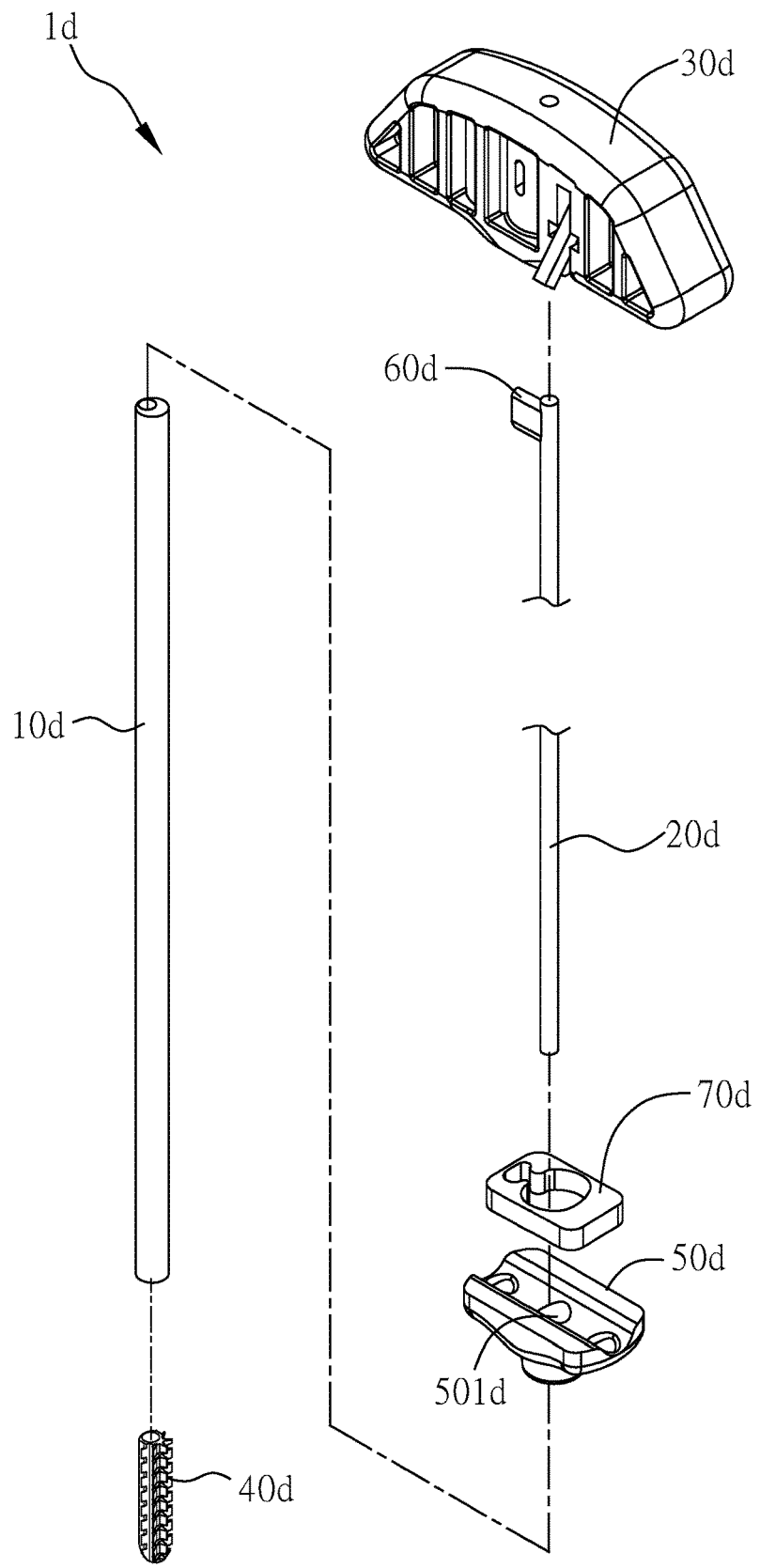
FIG. 11A is an exploded view of the eccentric reaming element according to yet another embodiment of the present disclosure.
Figure 11B:
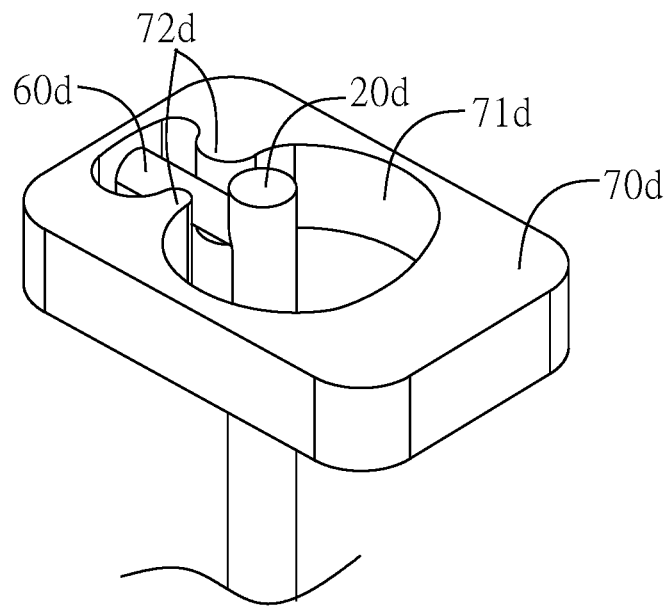
FIG. 11B is a partial schematic view of the combination of the eccentric shaft and the linkage element shown in FIG. 11A.

FIG. 11A is an exploded view of the eccentric reaming element according to yet another embodiment of the present disclosure. FIG. 11B is a partial schematic view of the combination of the eccentric shaft and the linkage element shown in FIG. 11A. In the preceding embodiment, the eccentric shaft 20 directly and fixedly connects to the operated element 30. Referring to FIG. 11A and FIG. 11B, in this embodiment, the operated element 30d is connected to the eccentric shaft 20d by other elements. The spinal reaming apparatus 1d further comprises a stressed arm 60d and a linkage element 70d, and preferably, the linkage element 70d is disposed inside the operated element 30d, and the linkage element 70d includes an accommodating slot 71d and forcing protrusions 72d. The stressed arm 60d connects to the eccentric shaft 20d and is disposed in the accommodating slot 71d. Specifically speaking, one end of the eccentric shaft 20d passes through the assembly hole 501d of the gripping element 50d and the sleeve 10d, thereby to connect to the eccentric reaming element 40d. The stressed arm 60d connects to another end of the eccentric shaft 20d, and part of the eccentric shaft 20d and the stressed arm 60d are both accommodated in the accommodating slot 71d of the linkage element 70d, as shown in FIG. 11B.

Furthermore, the forcing protrusions 72d project from the inner wall of the accommodating slot 71d toward the stressed arm 60d, and the forcing protrusions 72d are located on opposite sides of the stressed arm 60d. Further, the linkage element 70d connects the operated element 30d. When the operated element 30d is rotated, the linkage element 70d is rotated along with the operated element 30d. At this moment, the forcing protrusions 72d press the stressed arm 60d and cause the stressed arm 60d to rotate the eccentric shaft 20d. For example, if the operated element 30d is rotated in the clockwise direction, the linkage element 70d will be rotated in the clockwise direction along with the operated element 30d. Referring to FIG. 11B as an example, the forcing protrusion 72d located on the underside of the stressed arm 60 can push the stressed arm 60d to rotate in the clockwise direction. At this moment, the stressed arm 60d drives the eccentric shaft 20d to rotate in the clockwise direction within the sleeve 10d, and the eccentric shaft 20d drives the eccentric reaming element 40d to rotate relative to the sleeve 10. In this embodiment, the linkage element 70d includes the accommodating slot 71d and the forcing protrusion 72d, and the linkage element 70d is disposed inside the operated element 30d. In another embodiment, the accommodating slot 71d and the forcing protrusion 72d can be directly formed inside the operated element 30d, but the present disclosure is not limited thereto.

Figure 12:
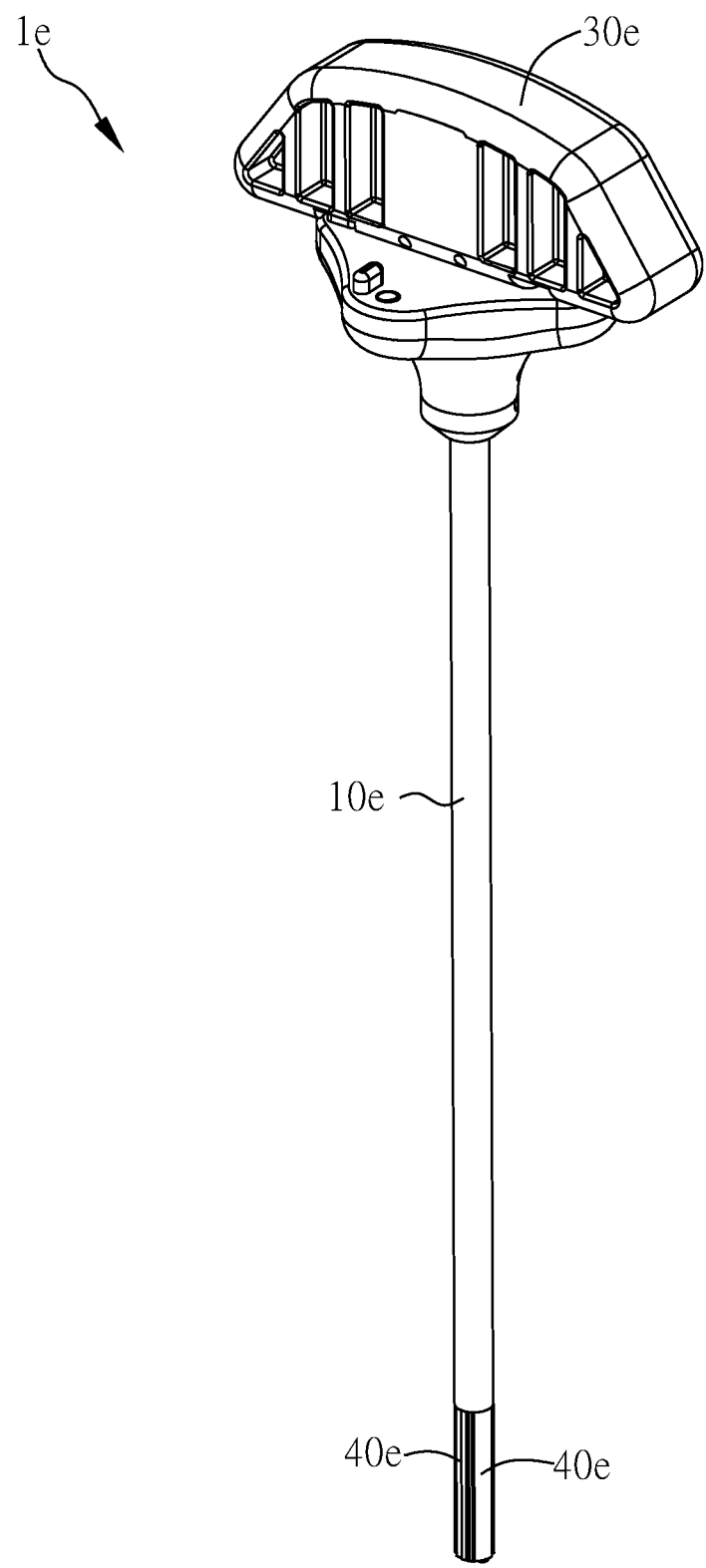
FIG. 12 is a perspective view of a spinal reaming apparatus according to yet another embodiment of the present disclosure.
Figure 13:
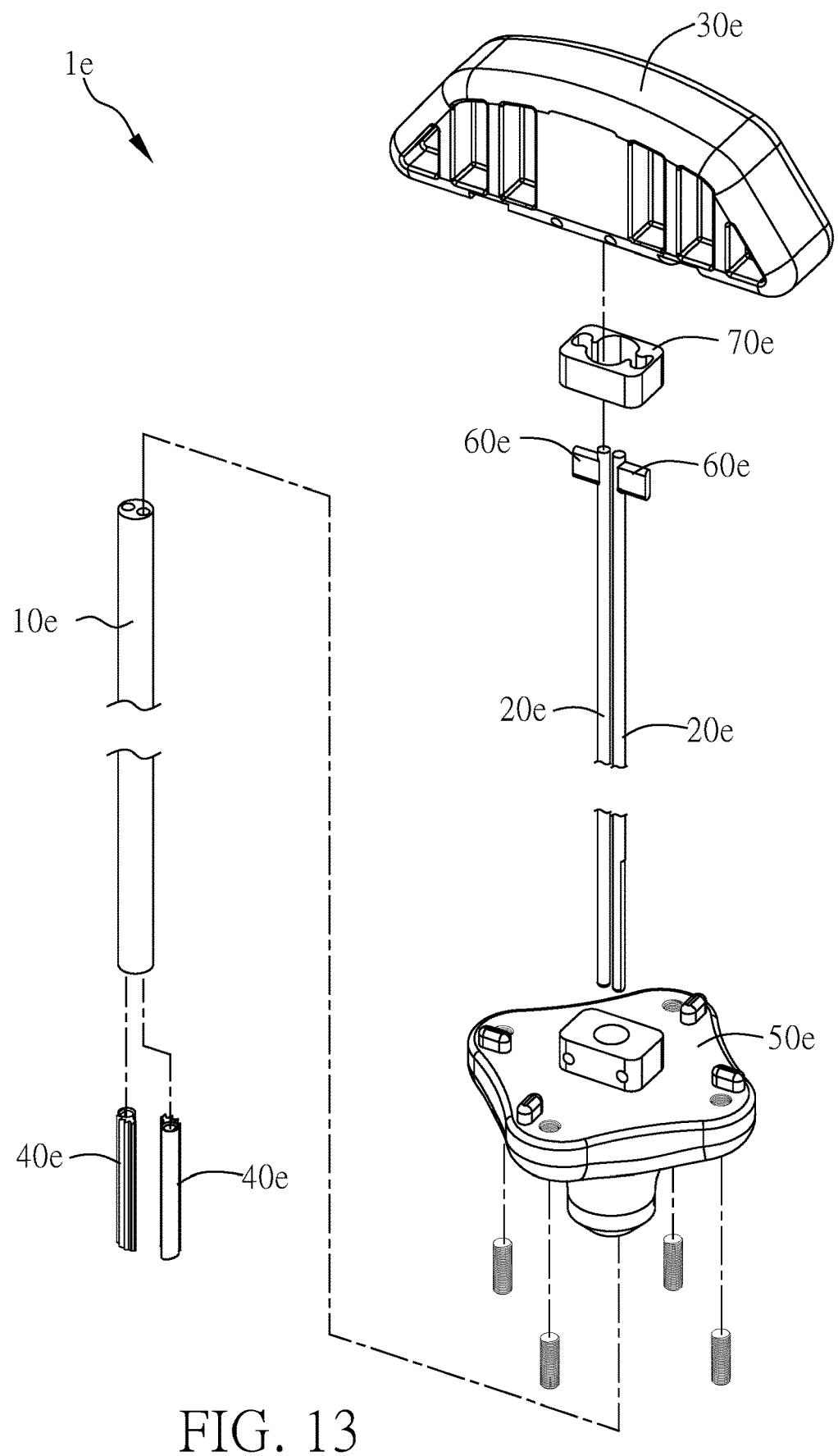
FIG. 13 is an exploded view of the spinal reaming apparatus shown in FIG. 12.

Furthermore, the spinal reaming apparatus of the preceding embodiment comprises one eccentric shaft and one eccentric reaming element, and the number of the eccentric shafts and the eccentric reaming elements can be more than one, as shown in FIG. 12 and FIG. 13, but the present disclosure is not limited thereto. FIG. 12 is a perspective view of a spinal reaming apparatus according to yet another embodiment of the present disclosure. FIG. 13 is an exploded view of the spinal reaming apparatus shown in FIG. 12. In this embodiment, a spinal reaming apparatus 1e comprises a sleeve 10e, two eccentric shafts 20e, an operated element 30e, two eccentric reaming elements 40e and a gripping element 50e. The two eccentric shafts 20e are disposed in the sleeve 10e, and both of the eccentric shafts 20e are passed through the sleeve 10e eccentrically. Hence, the sleeve 10e is not concentric with the two eccentric shafts 20e, nor do the projection of the axial center of the sleeve 10e and the projections of the axial centers of the two eccentric shafts 20e overlap.

Figure 14:
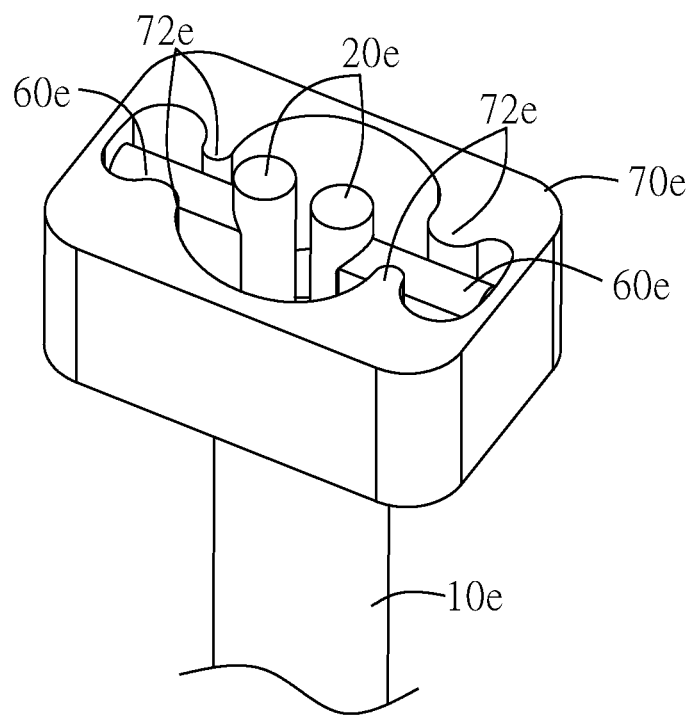
FIG. 14 is a partial schematic view of the combination of the sleeve, the eccentric shaft and the linkage element shown in FIG. 13.

In this embodiment, the reaming apparatus 1e further comprises two stressed arms 60e and a linkage element 70e, and the operated element 30e is connected to the two eccentric shafts 20e by the stressed arms 60e and the linkage element 70e. FIG. 14 is a partial schematic view of the combination of the sleeve, the eccentric shaft and the linkage element shown in FIG. 13. Referring to FIG. 14, the linkage element 70e includes an accommodating slot 71e and two forcing protrusions 72e. One end of the two eccentric shafts 20d pass through the gripping element 50e and the sleeve 10e to thereby connect to the two eccentric reaming elements 40d respectively. The two stressed arms 60e respectively connect to the other ends of the two eccentric shafts 20e, and portions of the eccentric shafts 20e and the stressed arm 60e are accommodated in the accommodating slot 71e. The two forcing protrusions 72e project from the inner wall of the accommodating slot 71e toward the two stressed arms 60e respectively. The linkage element 70e is connected to the operated element 30e, so the linkage element 70e is rotated along with the operated element 30e when the operated element 30e is rotated. At that moment, the two forcing protrusions 72e press the two stressed arms 60e respectively such that the stressed arms 60e drive the eccentric shafts 20 to rotate.

Figure 15B:
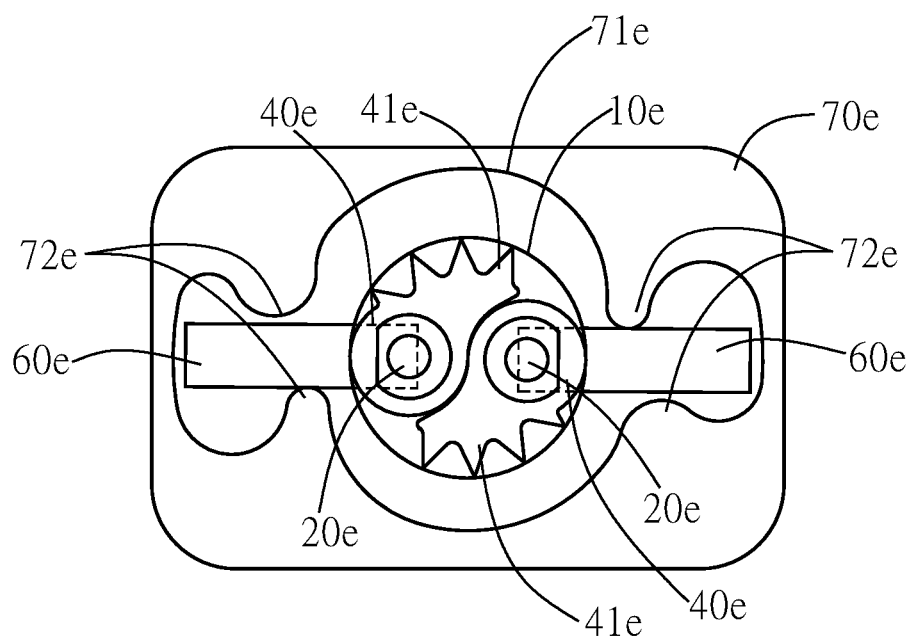
FIG. 15B is a bottom view of the combination of the sleeve, the eccentric shafts, the eccentric reaming elements, the stressed arms and the linkage element shown in FIG. 13 operating in the folded mode.

FIG. 15A is a bottom view of the spinal reaming apparatus shown in FIG. 12 operating in the folded mode. FIG. 15B is a bottom view of the combination of the sleeve, the eccentric shafts, the eccentric reaming elements, the stressed arms and the linkage element shown in FIG. 13 operating in the folded mode. Referring to FIG. 12, FIG. 15A and FIG. 15B, in this embodiment, the two eccentric reaming elements 40e are connected to the two eccentric shafts 20e respectively, and the combined outer diameter of two the eccentric reaming elements 40e is substantially equal to or smaller than an outer diameter of the sleeve 10e when the spinal reaming apparatus 1e is in the folded mode. Each of the eccentric reaming elements 40e includes a plurality of cutting portions 41e disposed on the outer surface of the eccentric reaming elements 40s. The combined outer diameter of the two eccentric reaming elements 40e is defined as the outer diameter of an imaginary cylinder formed by connecting the outermost edges of the cutting portions 41 of the two eccentric reaming elements 40e. The combined outer diameter of the two eccentric reaming elements 40 is equal to or smaller than the outer diameter of the sleeve 10e; hence, the two eccentric reaming elements 40 do not protrude from the outside of the sleeve 10e when the spinal reaming apparatus 1e is in the folded mode. Preferably, the combined outer diameter of the two eccentric reaming elements 40 is substantially equal to the outer diameter of the sleeve 10e, as shown in FIG. 15B.

Figure 16:
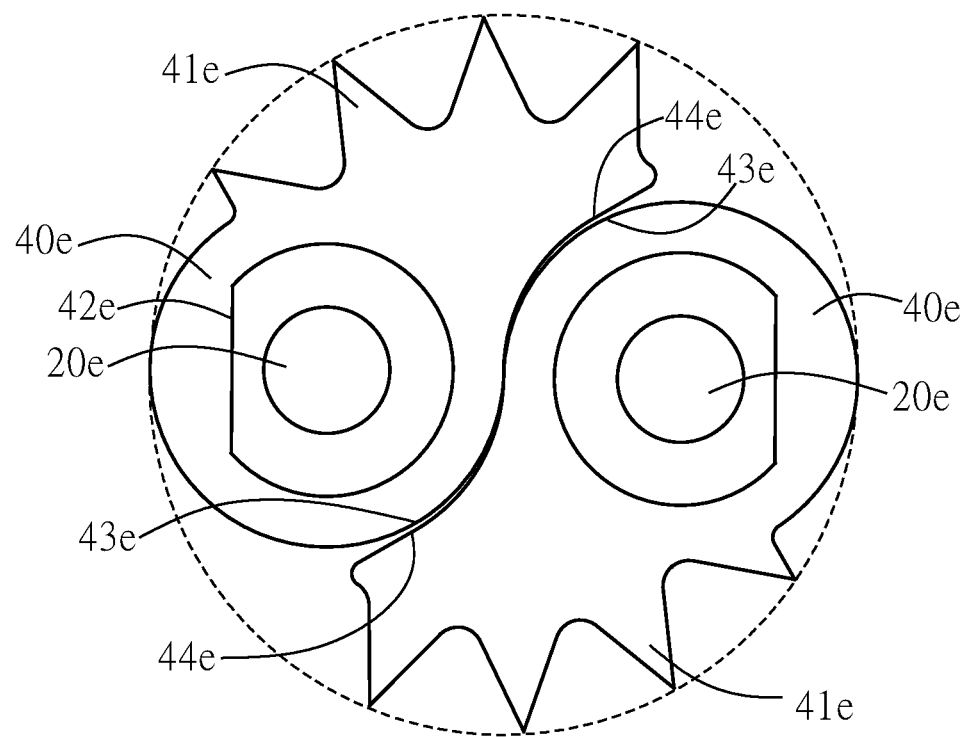
FIG. 16 is an enlarged view of the eccentric shafts and the eccentric reaming elements shown in FIG. 15B.

FIG. 16 is an enlarged view of an eccentric shaft and the eccentric reaming element shown in FIG. 15B. Referring to FIG. 16, preferably, the corresponding sides of the two eccentric reaming elements 40e are of configurations mutually matched to each other. For instance, each of the two eccentric reaming elements 40e comprises a protrusion 43e and a recess 44e, which are disposed on the corresponding sides of the two eccentric reaming elements 40e. When the spinal reaming apparatus 1e is in the folded mode, the recess 44e of one eccentric reaming element 40e is mutually matched with the protrusion 43e of another eccentric reaming element 40e such that the corresponding sides of the two eccentric reaming elements 40e can be fitted to each other.

In this embodiment, the first positioning portion 31e of the operated element 30e is two recesses 313e, 314e located on opposite sides of the operated element 30e. Correspondingly, two second positioning portions 51e, 52e are disposed on the surface (which is toward the operated element 30e) of the gripping element 50e, and the second positioning portions 51e, 52e are protrusions. As shown in FIG. 15A, this embodiment is exemplified by four recesses 313e, 314e (two sets of the first positioning portion 31e) and four second positioning portions 51e, 52e. Preferably, the surface of the gripping element 50e toward the operated element 30e is a square, and the positioning portions 51e (or 52e) are disposed adjacent to the four corners of the surface.

Figure 17A:
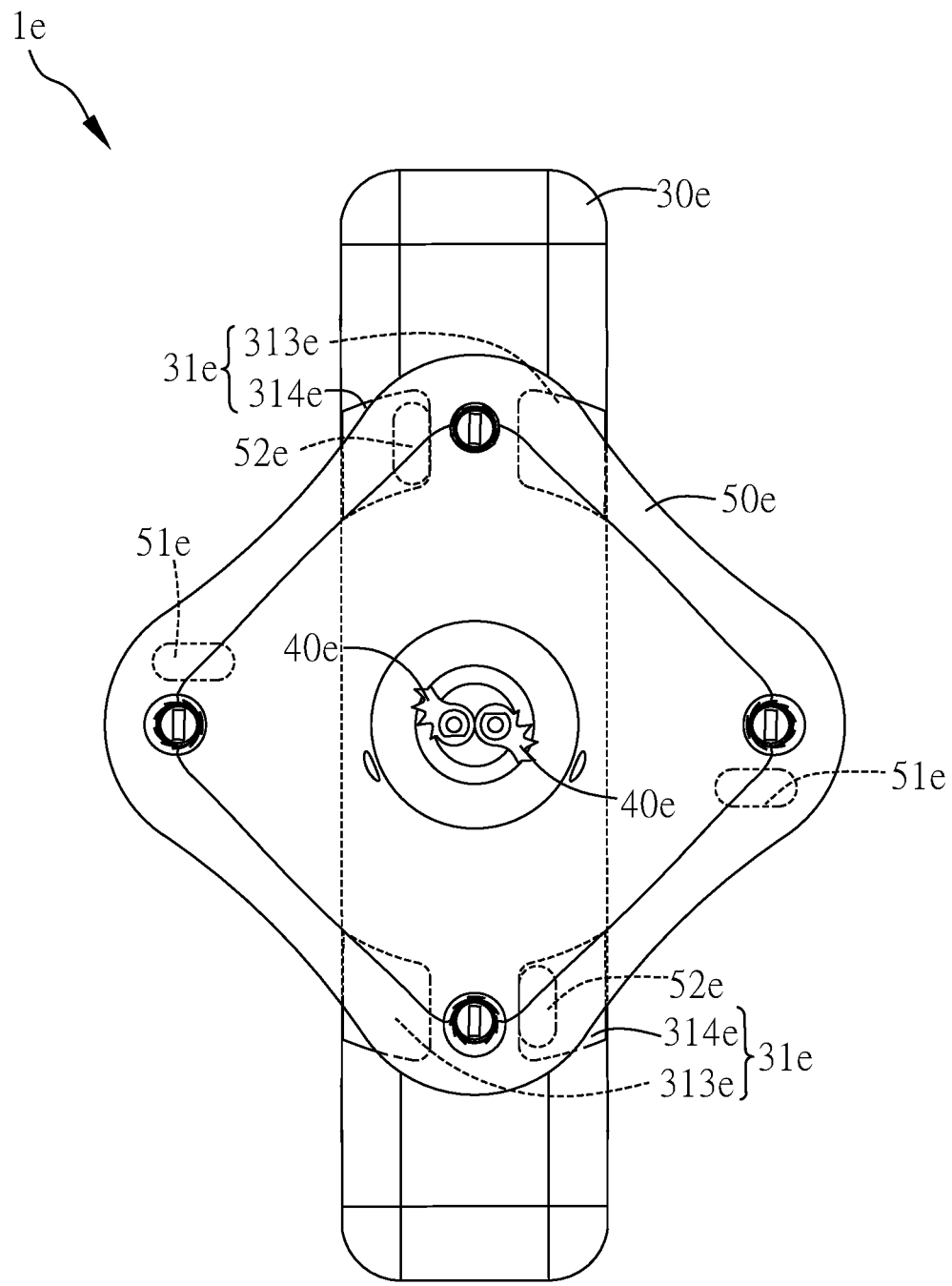
FIG. 17A is a bottom view of the spinal reaming apparatus shown in FIG. 12 operating in the functioning mode.
Figure 17B:
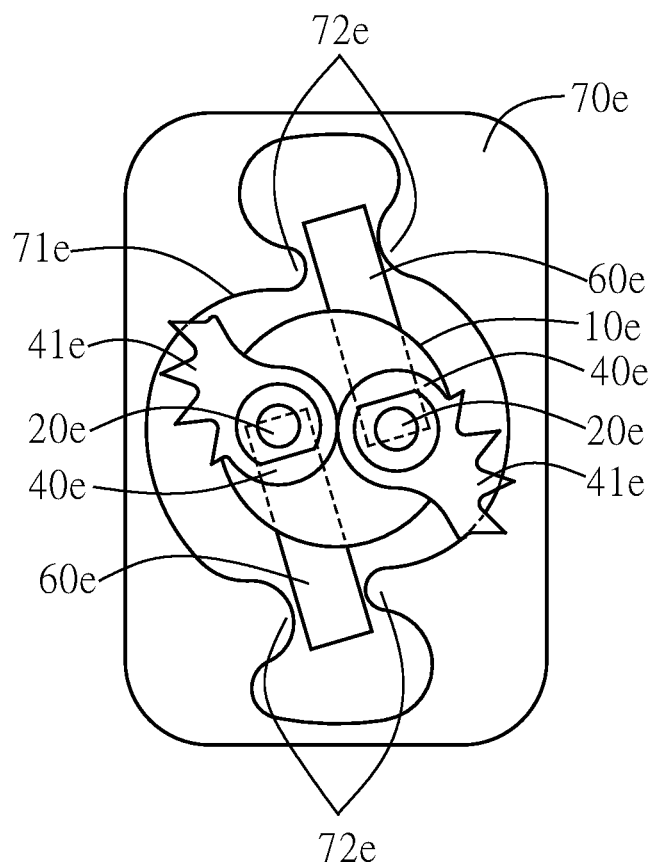
FIG. 17B is an enlarged view of the eccentric shafts, the eccentric reaming elements, the stressed arms and the linkage element shown in FIG. 15B.

The spinal reaming apparatus 1e is kept in the folded mode when the second positioning portion 51e of the gripping element 50e is accommodated in the recesses 313e of the first positioning portion 31e of the operated element 30e, as shown in FIG. 15A. When the surgeon needs to switch the spinal reaming apparatus 1e to the functioning mode, the surgeon rotates the operated element 30e by 90 degrees. Preferably, the operated element 30e is restricted from rotating 90 degrees in the counterclockwise direction through the disposition of the recesses 313e, 314e and the second positioning portions 51e, 52e (using FIG. 15A as an example). FIG. 17A is a bottom view of the spinal reaming apparatus shown in FIG. 12 operating in the functioning mode. FIG. 17B is an enlarged view of the eccentric shafts, the eccentric reaming elements, the stressed arms and the linkage element shown in FIG. 15B. As shown in FIG. 17A and FIG. 17B, when the operated element 30e is rotated, the two stressed arms 60e drive the two eccentric shafts 20e to rotate in the counterclockwise direction, and the two eccentric shafts 20e respectively drive the two eccentric reaming elements 40e to rotate in the counterclockwise direction and relative to the sleeve 10e, such that the cutting portions 41e of the two eccentric reaming elements 40e expand outward (protrude from the sleeve 10) to form the functioning mode. At this moment, the second positioning portions 52e of the gripping element 50e are accommodated in the recesses 314e of the first positioning portion 31e.

As described above, in the embodiments of the present invention, a spinal reaming apparatus comprises a sleeve, an eccentric shaft, an operated element and an eccentric reaming element. The eccentric shaft is disposed in the sleeve. The two opposing ends of the eccentric shaft are connected to an operated element and the eccentric reaming element, respectively. When the operated element is rotated, the operated element drives the eccentric reaming element to rotate relative to the sleeve on the eccentric shaft such that the spinal reaming apparatus will switch between a folded mode and a functioning mode. Therefore, the spinal reaming apparatus is able to not only passes through an anatomically narrow structure, such as the pedicle, in the folded mode, which is smaller (safer) in terms of size, but also performs a reaming procedure in an anatomically recipient structure, such as the cancellous bone in the vertebra, in the functioning mode, which is larger in terms of size, thereby reducing the risk of a rupture, which would otherwise be caused by any large surgical instrument.

The prior art has its drawbacks. For instance, in the prior art, an implanting channel is reamed with a bone drill or a surgical drill to increase its inner diameter to 6.5 mm to 7 mm so as to allow the implant to reach a desired expansion position inside a vertebra. However, the implant in the implanting channel is subjected to considerable compression. As a result, not only is the space within the implanting channel limited, thereby rendering manipulation inconvenient, but the chance of implant deformation or implanting channel deviation also increases. For instance, when the implant is initially expanded, either the supporting arms are subjected to overly strong forces and thus bent, leading to their deformation, or the implant is subjected to unequal forces and thus deviates from the planned implanting path. The aforesaid problems often happen to the upper arms of the supporting arms of the implant. Therefore, if the upper arms of the supporting arms are not in direct contact with any bone tissue from the very beginning, the aforesaid problems can be addressed. In this regard, one of the advantages of reaming the implanting channel with the spinal reaming apparatus of the present disclosure is described below. The reaming procedure is performed at an implant expansion position (for example, the cancellous bone) to form an implanting channel whose inner diameter is greater than the outer diameter of the implant, such that the upper arms of the supporting arms of the implant cannot come into contact with the osteo-wall of the implanting channel; hence, as soon as it expands, the implant is not immediately subjected to overly strong forces but can expand a little bit so as to prevent bend-associated deformation and deviation of the implant from the planned implanting path.

Regarding the objectives, means, and efficacy, the present disclosure is different from prior arts. The present disclosure is disclosed above by preferred embodiments. However, persons skilled in the art should understand that the preferred embodiments are illustrative of the present disclosure only and shall not be interpreted as restrictive of the scope of the present disclosure. Hence, all equivalent modifications and replacements made to the aforesaid embodiments shall fall within the scope of the present disclosure. Accordingly, the legal protection for the present disclosure shall be defined by the appended claims.

What is claimed is:

1. A spinal reaming apparatus, comprising:
   a sleeve having a first end and a second end opposing the first end;
   an eccentric shaft disposed in the sleeve;
   an operated element connected to the eccentric shaft and positioned proximate to the first end of the sleeve;
   an eccentric reaming element connected to the eccentric shaft and disposed at the second end of the sleeve, wherein, when the operated element is configured to be rotated, the operated element drives the eccentric reaming element to rotate relative to the sleeve on the eccentric shaft such that the spinal reaming apparatus switches between a folded mode and a functioning mode;
   a linkage element connected the operated element and including an accommodating slot and a forcing protrusion; and
   a stressed arm connected to the eccentric shaft and disposed in the accommodating slot,
   wherein the forcing protrusion projects from an inner wall of the accommodating slot toward the stressed arm, and when the operated element is configured to be rotated, the forcing protrusion presses the stressed arm.

2. The spinal reaming apparatus of claim 1, wherein the eccentric reaming element rotates eccentrically and relative to the sleeve with the eccentric shaft as a pivot.

3. The spinal reaming apparatus of claim 1, wherein the eccentric reaming element is substantially flush with the sleeve in the folded mode, and the eccentric reaming element protrudes from the sleeve in the functioning mode.

4. The spinal reaming apparatus of claim 1, wherein an outer diameter of the eccentric reaming element is substantially equal to an outer diameter of the sleeve.

5. The spinal reaming apparatus of claim 1, wherein the eccentric reaming element is of a first radius, and when the spinal reaming apparatus rotates a complete turn in the functioning mode, a second radius of a circular trajectory is formed by the eccentric reaming element, and the second radius is greater than the first radius.

6. The spinal reaming apparatus of claim 1, wherein the operated element is configured to be rotated relative to the sleeve by 90 degrees or 180 degrees such that the spinal reaming apparatus switches between the folded mode and the functioning mode.

7. The spinal reaming apparatus of claim 1, further comprising a gripping element disposed at the first end of the sleeve and between the sleeve and the operated element.

8. The spinal reaming apparatus of claim 7, wherein the eccentric shaft passes through the gripping element to connect to the operated element.

9. The spinal reaming apparatus of claim 7, wherein the operated element comprises a fastening unit for fixing a position of the operated element relative to the gripping element.

10. The spinal reaming apparatus of claim 7, wherein the operated element comprises a first positioning portion, and the gripping element comprises two second positioning portions, such that the first positioning portion can move from one of the two second positioning portions to the other said second positioning portion and engage therewith when the operated element is rotated.

11. The spinal reaming apparatus of claim 10, wherein the gripping element comprises a guide groove, the two second positioning portions are disposed at two opposing ends of the guide groove, respectively, and the first positioning portion moves along the guide groove when the operated element is rotated.

12. The spinal reaming apparatus of claim 10, wherein the first positioning portion comprises a pin and a lever, and the two second positioning portions are each a recess.

13. The spinal reaming apparatus of claim 1, wherein the eccentric reaming element is covered with a plurality of cutting portions.

14. The spinal reaming apparatus of claim 1, wherein the spinal reaming apparatus is configured to pass through a pedicle of a vertebra in the folded mode, and the spinal reaming apparatus is converted from the folded mode to the functioning mode after the spinal reaming apparatus reaches a vertebral body of the vertebra.

15. A spinal reaming apparatus, comprising:
   a sleeve having a first end and a second end opposing the first end;
   two eccentric shafts disposed in the sleeve;
   an operated element connected to the eccentric shaft and positioned proximate to the first end of the sleeve, wherein the operated element comprises an accommodating slot and two forcing protrusions;

two eccentric reaming elements connected to the two eccentric shafts respectively and disposed at the second end of the sleeve, wherein, when the operated element rotates, the operated element drives the two eccentric reaming elements to rotate relative to the sleeve on the two eccentric shafts, such that the spinal reaming apparatus switches between a folded mode and a functioning mode, and a combined outer diameter of the two eccentric reaming elements is substantially equal to or smaller than an outer diameter of the sleeve in the folded mode; and two stressed arms connected to the two eccentric shafts respectively and disposed in the accommodating slot, wherein the two forcing protrusions project from an inner wall of the accommodating slot toward the two stressed arms respectively, and when the operated element is configured to be rotated, the two forcing protrusions press the two stressed arms respectively.

16. The spinal reaming apparatus of claim 15, wherein corresponding sides of the two eccentric reaming elements are of configurations mutually matched to each other.

17. The spinal reaming apparatus of claim 16, wherein each of the two eccentric reaming elements comprises a protrusion and a recess, which are disposed on the corresponding sides of the two eccentric reaming elements, wherein, in the folded mode, the recess of one eccentric reaming element is mutually matched with the protrusion of another eccentric reaming element.

* * * * *